(12) United States Patent
Furlong

(10) Patent No.: US 11,812,933 B2
(45) Date of Patent: *Nov. 14, 2023

(54) ENDOSCOPIC TOOL FOR DEB RIDING AND REMOVING POLYPS

(71) Applicant: Interscope, Inc., Whitinsville, MA (US)

(72) Inventor: Cosme Furlong, Whitinsville, MA (US)

(73) Assignee: Interscope, Inc., Whitinsville, MA (US)

( * ) Notice: Subject to any disclaimer, the term of this patent is extended or adjusted under 35 U.S.C. 154(b) by 270 days.

This patent is subject to a terminal disclaimer.

(21) Appl. No.: 17/234,270

(22) Filed: Apr. 19, 2021

(65) Prior Publication Data

US 2021/0235975 A1    Aug. 5, 2021

Related U.S. Application Data

(63) Continuation of application No. 15/804,884, filed on Nov. 6, 2017, now Pat. No. 10,980,403, which is a
(Continued)

(51) Int. Cl.
*A61B 5/00* (2006.01)
*A61B 1/018* (2006.01)
(Continued)

(52) U.S. Cl.
CPC ............ *A61B 1/018* (2013.01); *A61B 1/31* (2013.01); *A61B 10/04* (2013.01);
(Continued)

(58) Field of Classification Search
CPC .......... A61B 1/018; A61B 1/31; A61B 10/04;
A61B 17/32002; A61B 2010/0225; A61B
2017/00553; A61B 2017/00818; A61B
2017/00862; A61B 2017/320032; A61B
2217/005; A61B 2217/007;
(Continued)

(56) References Cited

U.S. PATENT DOCUMENTS

D204,670 S     5/1966   Gilson
3,760,810 A    9/1973   Van Hoorn
(Continued)

FOREIGN PATENT DOCUMENTS

CN    1933761 A     3/2007
CN    202051784 U   11/2011
(Continued)

OTHER PUBLICATIONS

Chinese Foreign Action issued for CN Appl. Ser. No. 2018105988947 dated Jun. 3, 2021 (6 pages).
(Continued)

*Primary Examiner* — May A Abouelela
(74) *Attorney, Agent, or Firm* — Foley & Lardner LLP

(57) ABSTRACT

An improved endoscopic tool easily and efficiently obtains samples of multiple polyps from a patient by debriding one or more polyps and retrieving the debrided polyps without having to alternate between using a separate cutting tool and a separate sample retrieving tool and may be used with an endoscope.

19 Claims, 16 Drawing Sheets

Related U.S. Application Data continuation of application No. 13/336,491, filed on Dec. 23, 2011, now Pat. No. 9,808,146.

(60) Provisional application No. 61/566,472, filed on Dec. 2, 2011.

(51) Int. Cl.

| | | |
|---|---|---|
| *A61B 1/31* | (2006.01) | |
| *A61B 10/04* | (2006.01) | |
| *A61B 17/32* | (2006.01) | |
| *A61B 10/02* | (2006.01) | |
| *A61B 17/00* | (2006.01) | |

(52) U.S. Cl.
CPC . *A61B 17/32002* (2013.01); *A61B 2010/0225* (2013.01); *A61B 2017/00553* (2013.01); *A61B 2017/00818* (2013.01); *A61B 2017/00862* (2013.01); *A61B 2017/320032* (2013.01); *A61B 2217/005* (2013.01); *A61B 2217/007* (2013.01)

(58) Field of Classification Search
CPC .... A61B 2010/045; A61B 2017/00017; A61B 2017/00398
See application file for complete search history.

(56) References Cited

U.S. PATENT DOCUMENTS

| | | | | |
|---|---|---|---|---|
| 3,834,392 | A | 9/1974 | Lampman et al. | |
| 3,911,923 | A | 10/1975 | Yoon | |
| 4,222,380 | A | 9/1980 | Terayama | |
| 4,226,239 | A | 10/1980 | Polk et al. | |
| 4,257,419 | A | 3/1981 | Goltner et al. | |
| 4,548,201 | A | 10/1985 | Yoon | |
| 4,646,738 | A | 3/1987 | Trott | |
| 4,735,605 | A | 4/1988 | Swartz | |
| 4,756,309 | A | 7/1988 | Sachse et al. | |
| 4,763,667 | A * | 8/1988 | Manzo | A61M 25/01 604/173 |
| 4,834,729 | A * | 5/1989 | Sjostrom | A61B 17/32002 604/22 |
| 4,850,957 | A | 7/1989 | Summers | |
| 4,950,278 | A | 8/1990 | Sachse et al. | |
| 4,966,162 | A * | 10/1990 | Wang | A61B 10/04 600/565 |
| 5,108,381 | A | 4/1992 | Kolozsi | |
| 5,259,366 | A | 11/1993 | Reydel et al. | |
| 5,269,789 | A | 12/1993 | Chin et al. | |
| 5,287,845 | A | 2/1994 | Faul et al. | |
| 5,320,630 | A | 6/1994 | Ahmed | |
| 5,320,635 | A * | 6/1994 | Smith | A61B 17/32002 606/167 |
| 5,349,940 | A | 9/1994 | Takahashi et al. | |
| 5,417,697 | A | 5/1995 | Wilk et al. | |
| 5,423,834 | A | 6/1995 | Ahmed | |
| 5,431,645 | A * | 7/1995 | Smith | A61B 10/06 606/1 |
| 5,462,559 | A | 10/1995 | Ahmed | |
| 5,507,797 | A | 4/1996 | Suzuki et al. | |
| 5,529,580 | A * | 6/1996 | Kusunoki | A61B 17/32002 606/180 |
| 5,620,447 | A | 4/1997 | Smith et al. | |
| 5,662,671 | A | 9/1997 | Barbut et al. | |
| 5,690,660 | A | 11/1997 | Kauker et al. | |
| 5,695,511 | A * | 12/1997 | Cano | A61B 17/32002 606/1 |
| 5,782,748 | A * | 7/1998 | Palmer | A61B 10/06 606/205 |
| 5,871,453 | A * | 2/1999 | Banik | A61B 10/04 600/564 |
| 5,906,615 | A * | 5/1999 | Thompson | A61B 18/1485 606/49 |
| 5,938,680 | A * | 8/1999 | Ginn | A61B 17/00008 600/210 |
| 5,961,534 | A * | 10/1999 | Banik | A61B 10/06 600/562 |
| 6,001,112 | A | 12/1999 | Taylor | |
| 6,010,515 | A | 1/2000 | Swain et al. | |
| 6,059,719 | A | 5/2000 | Yamamoto et al. | |
| 6,068,603 | A * | 5/2000 | Suzuki | A61B 10/04 600/564 |
| D435,653 | S | 12/2000 | Niedospial et al. | |
| 6,165,764 | A | 12/2000 | Holmes et al. | |
| 6,193,672 | B1 * | 2/2001 | Clement | A61M 1/85 600/565 |
| 6,245,011 | B1 | 6/2001 | Dudda et al. | |
| 6,299,763 | B1 | 10/2001 | Ashman | |
| 6,386,663 | B1 | 5/2002 | Olson | |
| 6,392,982 | B1 | 5/2002 | Kobayashi et al. | |
| 6,397,126 | B1 | 5/2002 | Nelson | |
| 6,517,560 | B1 | 2/2003 | Toth et al. | |
| 6,572,578 | B1 | 6/2003 | Blanchard | |
| 6,585,694 | B1 * | 7/2003 | Smith | A61M 25/0084 604/164.12 |
| 6,632,182 | B1 * | 10/2003 | Treat | A61B 10/04 600/564 |
| 6,645,218 | B1 | 11/2003 | Cassidy et al. | |
| 6,666,854 | B1 * | 12/2003 | Lange | A61B 17/2909 606/1 |
| 6,689,146 | B1 | 2/2004 | Himes | |
| 6,740,030 | B2 | 5/2004 | Martone et al. | |
| D536,449 | S | 2/2007 | Nakajima et al. | |
| 7,247,161 | B2 | 7/2007 | Johnston et al. | |
| 7,276,074 | B2 | 10/2007 | Adams et al. | |
| D589,618 | S | 3/2009 | Hasebe | |
| D593,679 | S | 6/2009 | Bartlett et al. | |
| D598,545 | S | 8/2009 | Haines et al. | |
| 7,625,347 | B2 | 12/2009 | Burbank et al. | |
| 7,691,110 | B2 | 4/2010 | Secrest et al. | |
| D620,107 | S | 7/2010 | Bartlett et al. | |
| 7,857,784 | B2 * | 12/2010 | Schmidberger | A61B 1/12 604/102.03 |
| D635,668 | S | 4/2011 | Bartlett et al. | |
| 8,070,756 | B2 * | 12/2011 | Secrest | A61B 17/3421 606/115 |
| 8,070,762 | B2 * | 12/2011 | Escudero | A61M 25/09 606/108 |
| D655,002 | S | 2/2012 | Bast et al. | |
| 8,123,750 | B2 | 2/2012 | Norton et al. | |
| D655,413 | S | 3/2012 | Nino et al. | |
| 8,277,474 | B2 | 10/2012 | Norman et al. | |
| 8,343,047 | B2 | 1/2013 | Albrecht et al. | |
| 8,435,259 | B2 * | 5/2013 | Dierck | A61B 17/32002 606/170 |
| 8,475,484 | B2 | 7/2013 | Wulfman et al. | |
| 8,480,689 | B2 | 7/2013 | Spivey et al. | |
| 8,506,564 | B2 | 8/2013 | Long et al. | |
| 8,528,563 | B2 | 9/2013 | Gruber | |
| 8,574,254 | B2 * | 11/2013 | Hedstrom | A61B 17/32002 606/171 |
| 8,622,997 | B2 | 1/2014 | Shippert | |
| 8,696,621 | B2 | 4/2014 | Gunday et al. | |
| D720,452 | S | 12/2014 | Jordan | |
| 8,939,897 | B2 | 1/2015 | Nobis | |
| 9,005,220 | B2 | 4/2015 | Wallace et al. | |
| 9,028,424 | B2 | 5/2015 | Furlong et al. | |
| 9,033,864 | B2 | 5/2015 | Furlong et al. | |
| 9,033,895 | B2 | 5/2015 | Furlong et al. | |
| 9,095,367 | B2 * | 8/2015 | Olson | A61B 34/37 |
| 9,408,593 | B2 | 8/2016 | Furlong et al. | |
| D780,916 | S | 3/2017 | Ogura et al. | |
| D784,529 | S | 4/2017 | Steele et al. | |
| D791,941 | S | 7/2017 | Burachynsky et al. | |
| 9,955,991 | B2 * | 5/2018 | Riva | A61B 17/32002 |
| 10,265,055 | B2 | 4/2019 | Furlong et al. | |
| 10,299,818 | B2 * | 5/2019 | Riva | A61B 1/018 |
| D855,802 | S | 8/2019 | Marcoux et al. | |
| 11,033,255 | B2 | 6/2021 | Furlong et al. | |
| 2001/0013487 | A1 | 8/2001 | Kaendler | |

(56) References Cited

U.S. PATENT DOCUMENTS

| | | | |
|---|---|---|---|
| 2002/0007190 A1* | 1/2002 | Wulfman | A61B 17/320758 606/171 |
| 2002/0013570 A1 | 1/2002 | Ruegg et al. | |
| 2002/0058857 A1 | 5/2002 | Smith | |
| 2003/0055315 A1 | 3/2003 | Gatto et al. | |
| 2003/0097146 A1* | 5/2003 | Montalvo | A61B 10/06 606/205 |
| 2004/0147934 A1* | 7/2004 | Kiester | A61B 17/32002 606/171 |
| 2004/0162572 A1* | 8/2004 | Sauer | A61B 10/04 600/565 |
| 2005/0090848 A1 | 4/2005 | Adams | |
| 2005/0159767 A1 | 7/2005 | Adams et al. | |
| 2005/0272976 A1 | 12/2005 | Tanaka et al. | |
| 2006/0064113 A1 | 3/2006 | Nakao | |
| 2006/0229646 A1 | 10/2006 | Sparks | |
| 2007/0005002 A1 | 1/2007 | Millman et al. | |
| 2007/0038022 A1* | 2/2007 | Nakao | A61B 17/0469 600/104 |
| 2007/0100362 A1* | 5/2007 | Deng | A61B 17/1624 606/171 |
| 2007/0129705 A1 | 6/2007 | Trombley et al. | |
| 2007/0179535 A1* | 8/2007 | Morrissey | A61N 1/0424 606/2 |
| 2007/0197871 A1 | 8/2007 | Geitz et al. | |
| 2007/0203395 A1 | 8/2007 | Mikkaichi | |
| 2008/0082021 A1* | 4/2008 | Ichikawa | A61B 10/0096 600/104 |
| 2008/0183201 A1* | 7/2008 | Berberich | A61B 17/32002 606/180 |
| 2008/0194910 A1 | 8/2008 | Miyamoto et al. | |
| 2008/0234602 A1 | 9/2008 | Oostman et al. | |
| 2008/0249553 A1* | 10/2008 | Gruber | A61B 17/32053 606/171 |
| 2008/0290040 A1 | 11/2008 | Kane et al. | |
| 2009/0069806 A1* | 3/2009 | De La Mora Levy | A61B 17/072 606/198 |
| 2009/0234378 A1 | 9/2009 | Escudero et al. | |
| 2009/0240261 A1 | 9/2009 | Drews et al. | |
| 2010/0010525 A1 | 1/2010 | Lockard et al. | |
| 2010/0016757 A1* | 1/2010 | Greenburg | A61B 1/00096 600/7 |
| 2010/0021245 A1 | 1/2010 | Li | |
| 2010/0036375 A1 | 2/2010 | Regadas | |
| 2010/0048992 A1 | 2/2010 | Okada et al. | |
| 2010/0049225 A1 | 2/2010 | To et al. | |
| 2010/0081874 A1 | 4/2010 | Miyamoto et al. | |
| 2010/0121141 A1 | 5/2010 | Rontal | |
| 2010/0145374 A1* | 6/2010 | Perkins | A61F 9/00736 606/171 |
| 2010/0168512 A1 | 7/2010 | Rahmani | |
| 2010/0217245 A1* | 8/2010 | Prescott | A61B 17/1624 606/1 |
| 2010/0291536 A1 | 11/2010 | Viljoen et al. | |
| 2010/0298855 A1* | 11/2010 | Dierck | A61B 17/32002 606/170 |
| 2011/0106029 A1 | 5/2011 | Garren et al. | |
| 2011/0112364 A1* | 5/2011 | Rone | A61B 17/3474 600/114 |
| 2011/0118544 A1 | 5/2011 | Adams et al. | |
| 2011/0257477 A1 | 10/2011 | Mcweeney | |
| 2011/0257667 A1* | 10/2011 | Nakamura | A61B 17/12136 606/153 |
| 2011/0270126 A1* | 11/2011 | Gunday | A61B 10/0275 600/565 |
| 2011/0298209 A1 | 12/2011 | Nguyen et al. | |
| 2012/0109130 A1 | 5/2012 | Casey et al. | |
| 2012/0221035 A1 | 8/2012 | Harvey | |
| 2012/0226101 A1 | 9/2012 | Tinkham et al. | |
| 2012/0226103 A1 | 9/2012 | Gunday et al. | |
| 2013/0016316 A1 | 1/2013 | Cheng et al. | |
| 2013/0023770 A1 | 1/2013 | Courtney et al. | |
| 2013/0046313 A1 | 2/2013 | Sullivan et al. | |
| 2013/0046316 A1 | 2/2013 | Sullivan et al. | |
| 2013/0103067 A1 | 4/2013 | Fabro et al. | |
| 2013/0190561 A1 | 7/2013 | Oskin et al. | |
| 2013/0317529 A1 | 11/2013 | Golden et al. | |
| 2014/0100567 A1 | 4/2014 | Edwards et al. | |
| 2014/0155923 A1 | 6/2014 | Edwards et al. | |
| 2014/0236165 A1 | 8/2014 | Ries et al. | |
| 2014/0249448 A1 | 9/2014 | Furlong et al. | |
| 2015/0025541 A1 | 1/2015 | Furlong et al. | |
| 2015/0199795 A1 | 7/2015 | Naruse et al. | |
| 2017/0086801 A1 | 3/2017 | Furlong et al. | |
| 2017/0172396 A1 | 6/2017 | Nguyen et al. | |
| 2019/0183467 A1 | 6/2019 | Furlong et al. | |

FOREIGN PATENT DOCUMENTS

| | | |
|---|---|---|
| CN | 103648356 A | 3/2014 |
| CN | 104822331 B | 5/2017 |
| CN | 104220016 B1 | 6/2018 |
| DE | 33 39 322 A1 | 5/1984 |
| DE | 33 20 076 A1 | 12/1984 |
| DE | 19522403 A1 | 1/1997 |
| EP | 0 393 834 A2 | 10/1990 |
| EP | 0 609 084 A2 | 8/1994 |
| EP | 1 031 371 A1 | 8/2000 |
| EP | 1 586 275 | 10/2005 |
| EP | 1 875 871 A2 | 1/2008 |
| JP | H03-003314 | 1/1991 |
| JP | 05-220157 A | 8/1993 |
| JP | H06-269459 | 9/1994 |
| JP | S64-025833 | 8/1996 |
| JP | S64-025833 | 8/1996 |
| JP | 2002-503132 | 1/2002 |
| JP | 2003-524479 | 8/2003 |
| JP | 2005-253892 A | 9/2005 |
| JP | 2005-296412 A1 | 10/2005 |
| JP | 2009-172118 A | 8/2009 |
| JP | 2011-177231 A | 9/2011 |
| JP | 2012-511970 A | 5/2012 |
| JP | 2012-223590 | 11/2012 |
| JP | 2013-530774 A | 8/2013 |
| JP | 2014-128465 A | 7/2014 |
| JP | 5951919 B1 | 7/2016 |
| JP | 6392982 B2 | 9/2018 |
| WO | WO-94/10911 A1 | 5/1994 |
| WO | WO-95/30377 A1 | 11/1995 |
| WO | WO-99/11184 A1 | 3/1999 |
| WO | WO-01/22889 A1 | 4/2001 |
| WO | WO-03/079911 A1 | 10/2003 |
| WO | WO-2006/122279 | 11/2006 |
| WO | WO-2009/029430 A1 | 3/2009 |
| WO | WO-2012/075409 A1 | 6/2012 |
| WO | WO-2013/022525 | 2/2013 |
| WO | WO-2014/186736 A1 | 11/2014 |
| WO | WO-2016/161060 A1 | 10/2016 |

OTHER PUBLICATIONS

Examination Report issued for AU Appl. Ser. No. 2019271956 dated May 6, 2021 (4 pages).

Foreign Action other than Search Report on CA 2935859 dated Jan. 19, 2022.

Non-Final Office Action on U.S. Appl. No. 16/279,776 dated Sep. 23, 2021.

U.S. Office Action on U.S. Appl. No. 17/346,683 dated Oct. 21, 2021.

AU Office Action for AU Appl. No. 2017245419, dated Aug. 22, 2018.

Australian Examination Report for AU 2019271997 dated Sep. 14, 2020.

Australian Examination Report on AU 2017245419 dated Aug. 9, 2019.

Australian Examination Report on AU 2018214129 dated Jan. 8, 2020.

Australian Examination Report on AU 2019271956 dated May 11, 2020.

(56) References Cited

OTHER PUBLICATIONS

Canadian Examination Report on CA Application No. 2911545 dated Nov. 20, 2015.
Canadian Office Action CA Appln. 2935859 dated Mar. 8, 2021.
Chinese Office Action on CN 2018105988947 dated Sep. 2, 2020.
Chinese Office Action on CN Appln. 2017800288275 dated Jan. 25, 2021.
Declaration of Non-Establishment of International Search Report dated Jan. 8, 2016 in PCT Application No. PCT/US2015/052980.
EPO Examination Report on EP 17715304.6 dated Aug. 3, 2020.
European Search Report for application 17183220.7-1659 dated Nov. 3, 2017.
European Search Report on EP Appln. No. 15778839.9 dated Dec. 15, 2020.
European Search Report on EP 20175529.5 dated Nov. 11, 2020.
Examination Report for EP 12809398.6 dated Jul. 19, 2016.
Examination Report for EP 14731875.2 dated Aug. 17, 2016.
Examination Report No. 1 for Standard patent application for Application No. 2016201686, dated Mar. 1, 2017,4 pages.
Examination report No. 2 for Standard Patent Application for Application No. 2012345609 dated Jun. 4, 2017.
Examination Search Report for CA Application No. 2,964,001 dated Jun. 19, 2017.
Extended Search Report for EP Application No. 17195661.8 dated Feb. 27, 2018.
Final Office Action on U.S. Appl. No. 13/336,491 dated Mar. 2, 2016.
Final Office Action on U.S. Appl. No. 14/792,369 dated Jun. 5, 2018.
Final Office Action on U.S. Appl. No. 14/961,425 dated Aug. 3, 2018.
Final Office Action on U.S. Appl. No. 15/231,399 dated Apr. 24, 2019.
Final Office Action on U.S. Appl. No. 15/459,870 dated Mar. 10, 2020.
Final Office Action on U.S. Appl. No. 16/386,692 dated Oct. 22, 2019.
Final Office Action on U.S. Appl. No. 16/386,692 dated Dec. 4, 2020.
First Canadian Exam Report on CA 2935859 dated Apr. 22, 2020.
First Office Action for AU Appl. No. 2017248536, dated Sep. 12, 2018.
First Office Action for AU Appl. No. 2018214129, dated Jan. 16, 2019.
First Office Action for CA Appl. No. 2857671, dated Sep. 17, 2018.
First Office Action for CN Appl. No. 201580065244.0, dated Sep. 19, 2018.
First Office Action for CN Appl. No. 201710192152.X, dated Feb. 27, 2019.
First Office Action for European Patent Office Appl. No. 15778839.9, dated Feb. 1, 2019.
First Office Action for European Patent Office Appl. No. 15778840.7-1113, dated Feb. 1, 2019.
First Office Action for JP Appl. No. 2016-114249, dated Apr. 25, 2019.
First Office Action for JP Patent Office Appl. No. 2018-046515, dated Dec. 5, 2018.
First Office Action issued on Feb. 3, 2016 in Chinese Patent Application No. 201280068003.8.
Foreign Action other than Search Report on JP 2019-90628 dated Jun. 30, 2020.
Fourth Office Action for CN Application No. 201250068003.8 dated Nov. 3, 2017.
Intention to Grant for EP Appl. No. 17183220.7, dated Aug. 10, 2018.
International Preliminary Report and Written Opinion of the International Searching Authority for application No. PCT/US2015/052977 dated Apr. 4, 2017.
International Preliminary Report on Patentability (Chapter 1 of the Patent Cooperation Treaty)and Written Opinion of the International Searching Authority for Application No. PCT/US2015/052978 dated Apr. 4, 2017.
International Preliminary Report on Patentability and Written Opinion of the International Searching Authority for Application No. PCT/US2015/052979 dated Apr. 4, 2017.
International Preliminary Report on Patentability dated Nov. 26, 2015 in PCT Application No. PCT/US2014/038443.
International Preliminary Report on Patentability dated Jun. 12, 2014 in PCT Application No. PCT/US2012/067614.
International Search Report and Written Opinion dated May 28, 2013 in PCT App. No. PCT/US2012/067614.
International Search Report and Written Opinion for International Patent Application No. PCT/US2014/038443 dated Sep. 1, 2014.
International Search Report and Written Opinion for PCT/US2017/022536 dated Aug. 10, 2017.
International Search Report and Written Opinion for PCT/US2017/022536 dated Sep. 18, 2018.
International Search Report and Written Opinion of the International Searching Authority for International Application No. PCT/US2015/052977 dated Dec. 18, 2015.
International Search Report and Written Opinion of the International Searching Authority for International Application No. PCT/US2015/052979 dated Dec. 17, 2015.
International Search Report and Written Opinion of the International Searching Authority on International Application No. PCT/US2015/052978 dated Dec. 17, 2015.
Japanese Office Action for Patent App. No. 2017-517015 dated Apr. 3, 2018.
Japanese Office Action for application No. 2017-517005 dated Apr. 10, 2018.
Japanese Office Action on JP 2017-517011 dated Jan. 14, 2020.
Japanese Office Action on JP 2017-517011 dated Apr. 9, 2019.
Japanese Office Action on JP 2018-161103 dated Aug. 13, 2019.
Japanese Office Action on JP Appln.2019-90628 dated Mar. 23, 2021.
Non-Final Office Action on U.S. Appl. No. 15/231,399 dated Nov. 5, 2018.
Non-Final Office Action on U.S. Appl. No. 15/459,870 dated Sep. 25, 2019.
Non-Final Office Action on U.S. Appl. No. 15/459,870 dated Nov. 9, 2020.
Non-Final Office Action on U.S. Appl. No. 15/804,884 dated Mar. 4, 2020.
Non-Final Office Action on U.S. Appl. No. 16/386,692 dated Jun. 3, 2019.
Non-Final Office Action on U.S. Appl. No. 16/386,692 dated Jul. 1, 2020.
Non-Final Office Action on U.S. Appl. No. 29/545,290 dated Oct. 30, 2018.
Notice of Allowance on U.S. Appl. No. 14/792,369 dated Dec. 6, 2018.
Notice of Allowance on U.S. Appl. No. 14/961,425 dated Dec. 12, 2018.
Notice of Allowance on U.S. Appl. No. 15/231,399 dated Oct. 18, 2019.
Notice of Allowance on U.S. Appl. No. 15/459,870 dated Mar. 17, 2021.
Notice of Allowance on U.S. Appl. No. 15/804,884 dated Jul. 8, 2020.
Notice of Allowance on U.S. Appl. No. 15/804,884 dated Dec. 14, 2020.
Notice of Allowance on U.S. Appl. No. 16/386,692 dated Feb. 18, 2021.
Notice of Allowance on U.S. Appl. No. 29/545,289 dated Mar. 20, 2018.
Notice of Allowance on U.S. Appl. No. 29/545,290 dated Mar. 7, 2019.
Notification of Forthcoming Publication for EP Patent application No. 17183220.7 dated Jun. 26, 2019.
Notification of Reasons for Refusal for application 2017-517011 dated Apr. 3, 2018.

(56) References Cited

OTHER PUBLICATIONS

Office Action for CN2014800030452 dated Aug. 22, 2016.
Office Action for JP 2016-114249 dated Jun. 6, 2017.
Office Action for JP Application No. 2017-517005 dated Apr. 10, 2018.
Office Action for JP2008/0249553 dated Nov. 8, 2016.
Office Action for U.S. Appl. No. 14/792,369 dated Oct. 17, 2017.
Office Action in European Patent Application No. 14731875.2 dated Feb. 12, 2016.
Office Action on U.S. Appl. No. 13/336,491 dated Jan. 19, 2017.
Office Action on U.S. Appl. No. 13/336,491 dated Oct. 26, 2016.
Office Action on U.S. Appl. No. 14/961,425 dated Feb. 8, 2018.
Patent Examination Report for AU 2012345690 dated Jul. 22, 2016.
Search Report for CN2012800680038 dated Oct. 18, 2016.
Search Report for CN2014800030452 dated Aug. 22, 2016.
Second Office Action for CN2012800680038 dated Oct. 18, 2016.
Second Office Action on Cn 201710192152.X dated Oct. 24, 2019.
The EndoRotor Mucosal Resection System Procedural Guide, 2017, Interscope, Inc.LAB-0002 REV.
The EndoRotor Mucosal Resection System Procedural Guide, LAB-0005 2017 Interscope, Inc., 6 pages.
Third Chinese Office Action on CN 201710192152.X dated May 11, 2020.
Third Office Action for Application No. 201280068003.8 dated Apr. 17, 2017, 6 pages.
U.S. Notice of Allowance for U.S. Appl. No. 14/280,202 dated Oct. 7, 2014.
U.S. Notice of Allowance for U.S. Appl. No. 14/501,865 dated Feb. 20, 2015.
U.S. Notice of Allowance for U.S. Appl. No. 14/501,942 dated Mar. 18, 2015.
U.S. Notice of Allowance for U.S. Appl. No. 14/537,362 dated May 26, 2015.
U.S. Notice of Allowance in U.S. Appl. No. 14/501,957 dated Oct. 21, 2015.
U.S. Notice of Allowance on U.S. Appl. No. 13/336,491 dated Jul. 6, 2017.
U.S. Notice of Allowance on U.S. Appl. No. 13/336,491 dated Aug. 7, 2017.
U.S. Notice of Allowance on U.S. Appl. No. 14/316,203 dated Jun. 23, 2016.
U.S. Office Action for U.S. Appl. No. 13/336,491 dated Mar. 2, 2016.
U.S. Office Action for U.S. Appl. No. 13/336,491 dated Sep. 18, 2015.
U.S. Office Action for U.S. Appl. No. 14/280,202 dated Aug. 20, 2014.
U.S. Office Action for U.S. Appl. No. 14/316,203 dated Mar. 15, 2016.
U.S. Office Action for U.S. Appl. No. 14/501,865 dated Dec. 4, 2014.
U.S. Office Action for U.S. Appl. No. 14/501,932 dated Nov. 26, 2014.
U.S. Office Action for U.S. Appl. No. 14/501,942 dated Dec. 15, 2014.
U.S. Office Action for U.S. Appl. No. 14/501,957 dated Mar. 19, 2015.
U.S. Office Action for U.S. Appl. No. 14/501,957 dated Nov. 14, 2014.
U.S. Office Action for U.S. Appl. No. 14/537,362 dated Feb. 11, 2015.
U.S. Office Action on U.S. Appl. No. 13/336,491 dated May 11, 2016.
U.S. Office Action on U.S. Appl. No. 29/545,289 dated Oct. 31, 2017.
Australian Office Action issued for AU Appl. Ser. No. 2017235541 dated Jul. 29, 2021 (4 pages).
EP Office Action on EP Appl. Ser. No. 19162393.3 dated Feb. 17, 2023 (5 pages).
Examination Report on AU Appl. No. 2020202778, dated Aug. 24, 2022.
Extended European Search Report for EP Appl. No. 22166418.8, dated Jun. 24, 2022.
Foreign Action other than Search Report on AU 2020202778 dated Oct. 13, 2021.
Foreign Action other than Search Report on CN 2017800288275 dated Sep. 18, 2021.
Foreign Action other than Search Report on EP 15784187.5 dated Jun. 8, 2021.
Foreign Action other than Search Report on EP 20194941.9 dated Jul. 22, 2022.
Foreign Action other than Search Report on JP 2021-71768 dated Apr. 5, 2022.
Foreign Action other than Search Report on JP 2022-000823, dated Dec. 6, 2022.
JP Office Action on JP Appl. Ser. No. 2021-154126 dated Oct. 25, 2022 (6 pages).
Notice of Allowance on U.S. Appl. No. 16/390,791 dated May 9, 2022.
Notice of Allowance on U.S. Appl. No. 16/390,791 dated Nov. 2, 2022.
Notice of Allowance on U.S. Appl. No. 29/700,667 dated Mar. 10, 2022.
U.S. Office Action on U.S. Appl. No. 16/390,791 dated Jan. 7, 2022.

\* cited by examiner

ENDOSCOPIC TOOL FOR DEB RIDING AND REMOVING POLYPS

CROSS REFERENCE TO RELATED APPLICATIONS

This application is a continuation application of U.S. application Ser. No. 15/804,884, titled "ENDOSCOPIC TOOL FOR DEBRIDING AND REMOVING POLYPS," filed Nov. 6, 2017, which is a continuation application of U.S. application Ser. No. 13/336,491, titled, "ENDOSCOPIC TOOL FOR DEBRIDING AND REMOVING POLYPS," filed Dec. 23, 2011, which application claims priority to U.S. Application No. 61/566,472, titled, "ENDOSCOPIC TOOL FOR DEBRIDING AND REMOVING POLYPS," filed Dec. 2, 2011, all of which are hereby incorporated by reference in their entireties.

BACKGROUND OF THE INVENTION

Colon cancer is the third leading cause of cancer in the United States but is the second leading cause of cancer-related deaths. Colon cancer arises from pre-existing colon polyps (adenomas) that occur in as many as 35% of the US population. Colon polyps can either be benign, precancerous or cancerous. Colonoscopy is widely regarded as an excellent screening tool for colon cancer that is increasing in incidence worldwide. According to the literature, a 1% increase in colonoscopy screening results in a 3% decrease in the incidence of colon cancer. The current demand for colonoscopy exceeds the ability of the medical system to provide adequate screening. Despite the increase in colon cancer screening the past few decades, only 55% of the eligible population is screened, falling far short of the recommended 80%, leaving 30 million patients at risk.

Due to the lack of adequate resources, operators performing an colonoscopy typically only sample the largest polyps, exposing the patient to sample bias by typically leaving behind smaller polyps that could advance to colon cancer prior to future colonoscopy. Because of the sample bias, a negative result from the sampled polyps does not ensure the patient is truly cancer-free. Furthermore, operators are not incentivized to remove more polyps since the reimbursement is not based on the number of polyps removed or the adequacy of resection of any particular polyp. Existing polyps removal techniques are cumbersome and time consuming, and not reimbursed at a higher level.

At present, colon polyps are removed using a snare that is introduced into the patient's body via a working channel defined within an endoscope. The tip of the snare is passed around the stalk of the polyp to cut the polyp from the colon wall. Once the cut has been made, the cut polyp lies on the intestinal wall of the patient until it is retrieved by the operator as a sample. To retrieve the sample, the snare is first removed from the endoscope and a biopsy forceps is fed through the same channel of the endoscope to retrieve the sample. The limiting factor for patient access to colonoscopy is the amount of time required to complete procedures where patients have colon polyps.

Accordingly, there is a need for an improved endoscopic tool that increases the precision and speed of polyp removal for biopsy.

SUMMARY OF THE INVENTION

An improved endoscopic tool is provided that can easily and efficiently obtain samples of multiple polyps from a patient. In particular, the improved endoscopic tool is capable of debriding one or more polyps and retrieving the debrided polyps without having to alternate between using a separate cutting tool and a separate sample retrieving tool. The sampling can be integrated with colonoscopy inspection.

In one aspect, an endoscopic biopsy retrieval tool adapted for use with an endoscope a housing, a debriding component coupled to the housing, and a sample retrieval conduit disposed within the housing for retrieving debrided material that is debrided by the debriding component. In various embodiments, an improved endoscope may be configured with an integrated endoscopic biopsy retrieval tool that includes a debriding component and a sample retrieval conduit for retrieving debrided material that is debrided by the debriding component.

In another aspect, a method of retrieving polyps from a patient's body includes disposing an endoscopic tool within an instrumentation channel of an endoscope, inserting the endoscope in a patient's body, actuating a debriding component of the endoscopic tool to cut a polyp within the patient's body, and actuating a sample retrieval component of the endoscopic tool to remove the cut polyp from within the patient's body.

In yet another aspect, An endoscope includes a first end and a second end separated by a flexible housing. An instrumentation channel extends from the first end to the second end and an endoscopic tool is coupled to the instrumentation channel at the first end of the endoscope. The endoscopic tool includes a debriding component and a sample retrieval conduit partially disposed within the instrumentation channel.

This Summary is provided to introduce a selection of concepts in a simplified form that are further described below in the Detailed Description. This Summary is not intended to identify key features or essential features of the claimed subject matter, nor is it intended that this Summary be used to limit the scope of the claimed subject matter. Furthermore, the claimed subject matter is not limited to implementations that offer any or all advantages or solve any or all state of the art problems.

BRIEF DESCRIPTION OF THE DRAWINGS

The present disclosure is illustratively shown and described in reference to the accompanying drawing in which.

DETAILED DESCRIPTION

Technologies provided herein are directed towards an improved endoscopic tool that can easily and efficiently obtain samples of multiple polyps from a patient. In particular, the improved endoscopic tool is capable of debriding samples from one or more polyps and retrieving the debrided samples without having to remove the endoscopic tool from the treatment site within the patient's body.

Presently, physicians typically use a snare device that is capable of cutting polyps grown within the patient's body. The snare device, however, is not capable of retrieving the cut polyps. As such, in order for a physician to remove polyps from within a patient's body, the physician has to insert the snare device through the working channel of an endoscope, cut the polyps desired to be cut by the physician and leave the cut polyp at or around the surgical site within the patient's body and then remove the snare device from the working channel. Once the snare device is removed, the physician then inserts a sample retrieving device, such as forceps, and removes the cut polyps from the surgical site by grasping the cut polyp and removing the forceps from the working channel of the endoscope and releasing the cut polyp outside the patient's body. To avoid contaminating the cut polyps, the physician may remove cut polyps one at a time. As one can imagine, this is a very inefficient and time consuming process, while at the same time, may not allow the physician to identify a particular location within the patient's body a particular retrieved polyp had grown. As a result, if any of the retrieved polyps is determined to be cancerous, the physician may not be able to determine the location from which the cancerous polyp was removed hence complicating treatment planning.

The present disclosure will be more completely understood through the following description, which should be read in conjunction with the drawings. In this description, like numbers refer to similar elements within various embodiments of the present disclosure. Within this description, the claims will be explained with respect to embodiments. The skilled artisan will readily appreciate that the methods, apparatus and systems described herein are merely exemplary and that variations can be made without departing from the spirit and scope of the disclosure.

Figure 1:
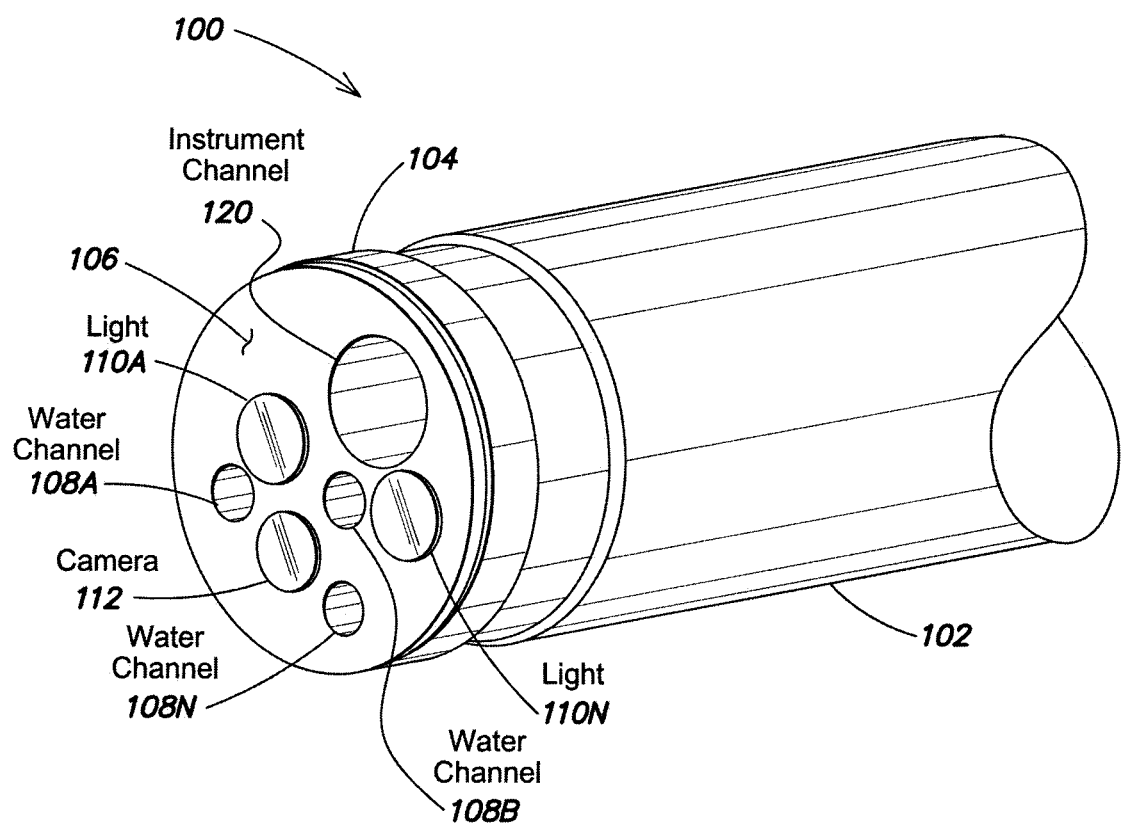
FIG. 1 illustrates a perspective partial view of an endoscope according to embodiments of the present disclosure.

Referring now to the drawings, FIG. 1 illustrates a perspective partial view of an endoscope according to embodiments of the present disclosure. Although the present disclosure is directed towards endoscopic tools adapted for use with any type of endoscope, for sake of convenience, the teachings of the present disclosure are directed towards endoscopic tools used with a lower GI scope, such as a colonoscope. It should, however, be appreciated that the scope of the present disclosure is not limited to endoscopic tools for use with GI scopes, but extends to any type of endoscope, including but not limited to gastroscopes and laryngoscopes, or other medical devices that may be used to treat patients.

According to various embodiments, a typical lower GI scope 100 includes a flexible body portion that extends from a first end or head portion 102 to a second end or handle portion. The head portion 102 may be configured to swivel so as to orient a tip 104 of the head portion 102 in any direction within a hemispherical space. The handle portion (not shown) has controls that allows the operator of the endoscope 100 to steer the colonoscope towards an area of interest within the colon and turn the corners between colon segments with two steering wheels.

A series of instruments reside on the face 106 of the scope's tip 104, including but not limited to, one or more water channels 108A-N, generally referred to as water channels 108, for irrigating the area with water, one or more light sources 110A-N, generally referred to as light sources 110, a camera lens 112, and an instrument channel 120 through which an endoscopic tool can be passed through to conduct a number of operations. The instrumentation channel 120 can vary in size based on the type of endoscope 100 being used. In various embodiments, the diameter of the instrumentation channel 120 can range from 3.2 mm to 4 mm. Some larger scopes may have two instrumentation channels 120 so that two tools can be passed into the patient simultaneously. However, larger scopes may cause discomfort to the patient and may be too large to enter the patient's body through some of the smaller cavities.

Figure 2B:
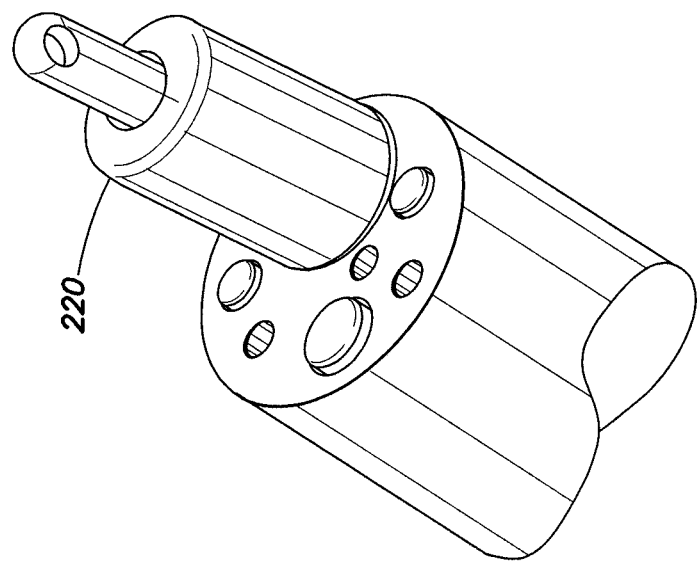
FIGS. 2A and 2B illustrate side perspective views of an endoscopic tool coupled with the endoscope shown in FIG. 1 according to embodiments of the present disclosure.
Figure 2A:
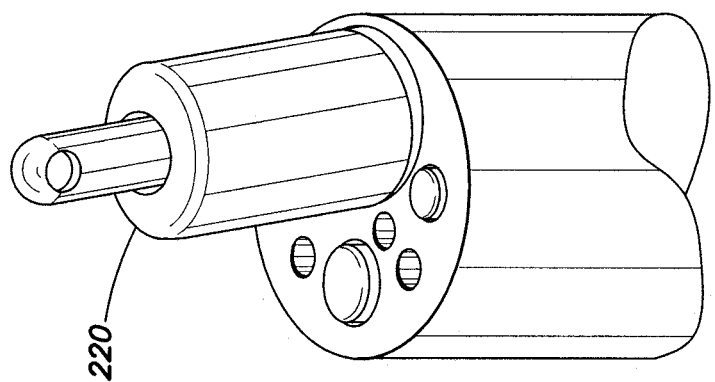
Figure 3B:
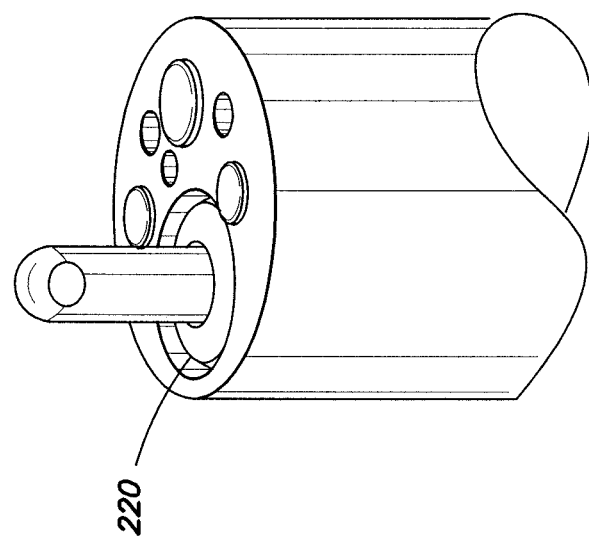
FIGS. 3A and 3B illustrate side perspective views of an alternate endoscopic tool coupled with the endoscope shown in FIG. 1 according to embodiments of the present disclosure.
Figure 3A:
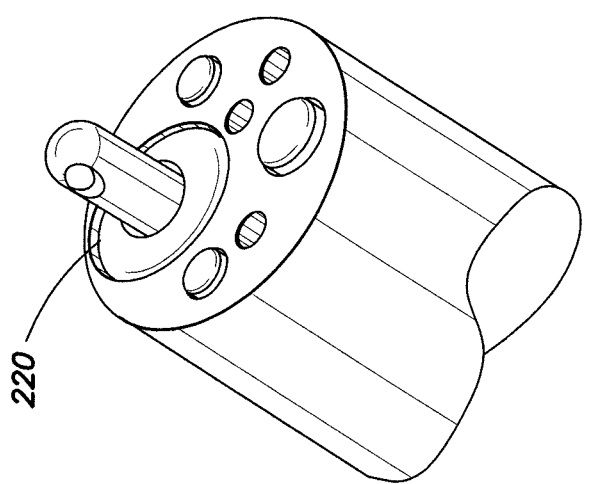

FIGS. 2A and 2B and 3A and 3B illustrate side perspective views of an endoscopic tool coupled with the endoscope shown in FIG. 1 according to embodiments of the present disclosure. The endoscopic tool 220 is configured to be fed through the instrumentation channel 120 of the endoscope 100. As shown in FIGS. 2A and 2B, the endoscopic tool 220 is capable of extending outside the tip 104 of the endoscope 100, while FIGS. 3A and 3B show that the endoscope tool 220 can be retracted within the endoscope such that no part of the endoscopic tool 220 is extending beyond the tip 104 of the endoscope 100. As will be described in further detail with respect to FIG. 4, the endoscopic tool 220 is capable of cutting or debriding a polyp as well as obtaining the debrided polyp from the surgical site without having to remove the endoscopic tool 220 from the endoscope 100.

Figure 4A:
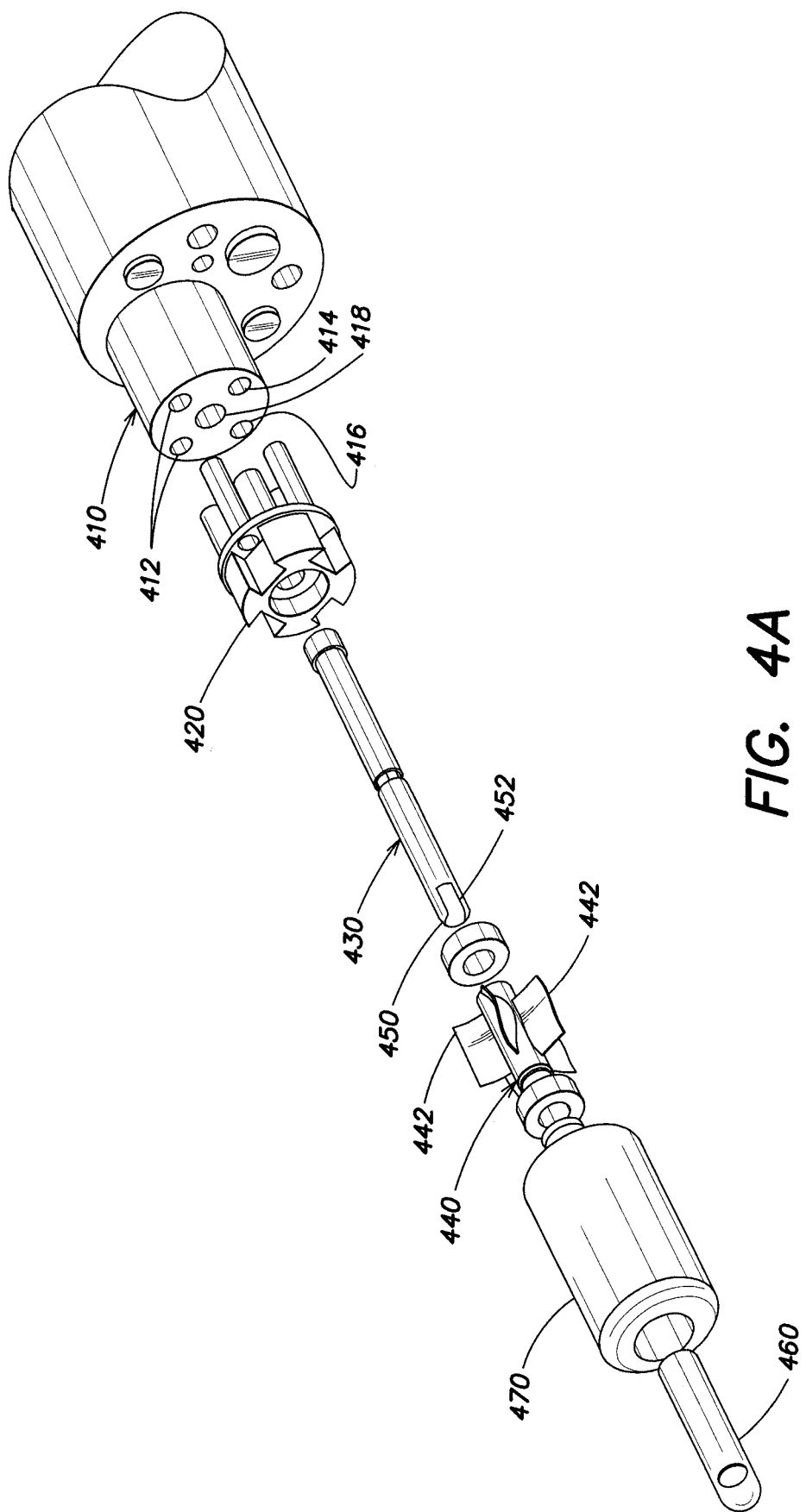
FIG. 4A illustrates an exploded view of the endoscopic tool that can be coupled with the endoscope according to embodiments of the present disclosure.

FIG. 4A illustrates an exploded view of the endoscopic tool 220 adapted for use with the endoscope 100 according to embodiments of the present disclosure. The endoscopic tool 220 includes a debriding component for debriding polyps grown in the patient's body, and a sample retrieval component for retrieving the debrided polyps from the surgical site. The endoscopic tool includes a tubing 410 coupled to a cap 420. In various embodiments, the cap 420 may be sealingly engaged with the tubing 410. The cap is coupled to a spindle 430 at a first portion of the spindle 430. In various embodiments, the spindle 430 may be at least substantially hollow. The spindle 430 is coupled to a rotor 440, which is configured to rotate the spindle 430. A second portion of the spindle 430 includes an inner blade 450 that may be configured to interact with an outer blade 460. The outer blade 460 is separated from the inner blade by an irrigation channel (not shown). A casing 470 is configured to encompass the cap 420 and the rotor 440, as shown above with respect to FIGS. 2A and 3A. It should be appreciated that other components, such as washers, bearings, seals, and the like, may be included in the endoscopic tool 220.

Figure 4B:
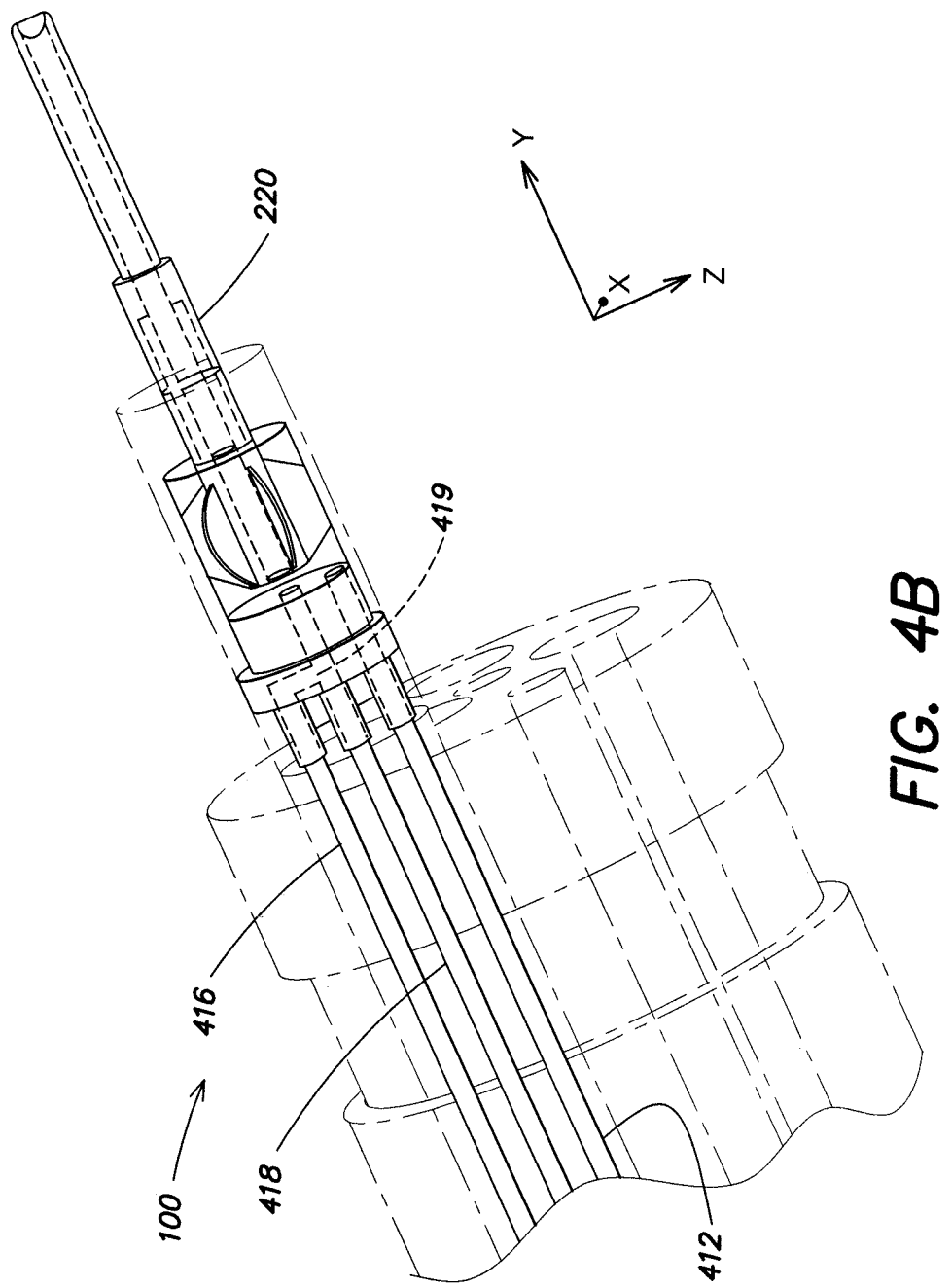
FIG. 4B illustrates a perspective view diagram of the endoscopic tool coupled to the endoscope illustrating the various conduits associated with the endoscopic tool.

FIG. 4B is a schematic diagram of a full endoscope including the endoscopic tool or tube tool for insertion into an inspection area via body cavity investigation or endoscopic surgery channel showing good combination of viewing, lighting, the description of distal elements by proximal end adjustment, etc. In various embodiments, the cap, connector, rotor and casing may be made from injection molded plastic. The spindle and the cannula may be made from surgical grade steel, and the tubing may be made from silicone. However, it should be appreciated that these materials are merely examples of materials that can be used. Those skilled in the art will appreciate that alternate materials may be used instead of the ones described above.

The tubing 410 in FIG. 4A may be sized to pass through the instrumentation channel 120 of the endoscope 100 in FIGS. 4A and 4B. The tubing 410 may include one or more pneumatic fluid entry conduits 412, one or more pneumatic fluid exit conduits 414, one or more irrigation conduits 416, and one or more suction conduits 418. The pneumatic fluid entry conduits 412 are configured to supply pressurized air to pneumatically drive the rotor 440, while the pneumatic fluid exit conduits 414 remove the air supplied by the pneumatic fluid entry conduits 412 to prevent a large amount of air from entering the patient's body. The irrigation conduits 416 supply an irrigation fluid, such as water, between the inner blade 450 and the outer blade 460 to help lubricate the area between the inner blade 450 and the outer blade 460. In addition, the irrigation fluid then flows from the outside of the inner blade 450 to the inside portion of the inner blade 450. It should be appreciated that the inside portion of the inner blade 450 may be coupled to the suction conduit 418 of the tubing 410 via the cap 420. The irrigation fluid that flows through the inside portion of the inner blade 450 and the suction conduit 418 helps lubricate the suction conduit 418, through which the debrided polyps and other waste from the patient's body are removed. As described above, the tubing 410 is coupled to the cap 420 at a first end, but is coupled to one or more components at a second end (not shown). For instance, at the second end, the pneumatic air entry conduits 412 may be coupled to a compressed air source, while the irrigation fluid conduit 416 may be coupled to a water supply source. In addition, the pneumatic fluid exit conduits 414 may be coupled to the compressed air source or simply left exposed outside the patient's body for venting.

In various embodiments, the suction conduit 418 may be coupled to a disposable cartridge that is configured to catch the cut polyps and store them for examination at a later time. In various embodiments, the disposable cartridge may include multiple collection bins. The operator may be capable of selecting the collection bin in which to collect a sample of a particular cut polyp. Upon selecting the collection bin, the suction conduit 418 supplies the collected material from within the patient's body to the particular collection bin. As such, the operator may be able to collect samples for each polyp in individual collection bins. In this way, the cancerous nature of individual polyps can be determined.

The cap 420 may be sized to fit within the first end of the tubing 410. In various embodiments, the first end of the tubing 410 may include a connector that is configured to couple with the cap 420. In various embodiments, the cap 420 may be press fitted into the connector of the tubing 410. As such, the cap 420 may include corresponding conduits that match the conduits of the tubing 410. Accordingly, compressed air from the compressed air source may be supplied through the pneumatic air entry conduits 412 of the tubing 410 and corresponding pneumatic air entry conduits of the cap 420 towards the rotor 440. The rotor 440 may include one or more rotor blades 442 on which the compressed air is impinged thereby causing the rotor 440 to rotate. The air impinging on the rotor blades 442 may then exit through the corresponding pneumatic air exit conduits of the cap and the pneumatic air entry conduits 414 of the tubing 410. The speed at which the rotor 440 can rotate depends on the amount of air and the pressure at which the air is supplied to the rotor 440. In various embodiments, the speed at which the rotor 440 rotates may be controlled by the operator of the endoscope 100. Although the present disclosure discloses pneumatic means for operating the rotor, alternate embodiments may include hydraulic means for operating the rotor. In such embodiments, a fluid, such as water, may be supplied in lieu of compressed air, in the pneumatic air entry conduit 412.

As described above, the spindle 430 is coupled to the rotor 440, such that when the rotor 440 rotates, the spindle 430 also rotates. In various embodiments, the first end of the spindle 430 includes the inner blade 450, which correspondingly, also rotates along with the rotor 440. The inner blade 450 may be sized to fit within the diameter of the outer blade 460. In various embodiments, irrigation fluid supplied from an irrigation fluid source may be supplied through the irrigation fluid conduit 416 of the tubing 410 and the corresponding conduit of the cap 420, along the space between the inner blade 450 and the outer blade 460, and into the suction conduit 418 defined by the inner diameter of the inner blade 450. It should be appreciated that since the suction conduit 418 is coupled to a vacuum source, fluids and other material may be suctioned through the suction conduit. In this way, the irrigation fluid is able to lubricate at least a substantial length of the suction conduit 418, from the tip 452 of the inner blade 450, through the spindle 430, cap 420, and tubing 410 into the disposable cartridge described above.

The inner blade 450 may rotate relative to the outer blade 460 such that the interaction between the inner blade 450 and the outer blade 460 causes polyps to be cut upon contact with the inner blade 450. In various embodiments, other mechanisms for cutting polyps may be utilized, which may or may not include the use of a rotor 440, inner blade 450 or outer blade 460.

The debriding component may generally be configured to debride a polyp. The term debride may be defined herein to refer to any action involving detaching the polyp from a surface of the patient's body. Accordingly, actions, including but not limited to, cutting, snaring, shredding, slicing, shattering, either entirely or partially, are also considered to lie within the definition of the term debride. Accordingly, the debriding component may be a component that is capable of cutting, snaring, shredding, slicing, shattering, a polyp from a surface of the patient's body. As such, the debriding component may be implemented as a forceps, scissor, knife, snare, shredder, or any other component that can debride a polyp. In some embodiments, the debriding component may be manually actuated such that the debriding component may be operated through the translation of mechanical forces exerted by an operator or automatically actuated, using a turbine, electrical motor, or any other force generating component to actuate the debriding component. For instance, the debriding component may be actuated hydraulically, pneumatically, or electrically. In various embodiments, a separate conduit passing through the tubing or a channel of the endoscope may he configured to carry an electrical wire to provide power to the electrically powered actuator, such as an electrical motor.

According to various embodiments, the debriding component may include a turbine assembly, which is made up of the rotor 440, the rotor blades 442, and the spindle 430. The operator may actuate the debriding component of the endoscopic tool by supplying compressed air to the turbine assembly. When the operator is ready to begin debriding the polyp, the operator actuates the turbine assembly causing the debriding component to be actuated. In embodiments, such as the embodiment disclosed in FIG. 4, actuating the debriding component may constitute causing the inner blade 450 to rotate relative to the outer blade 460. Upon actuation, the operator may bring the endoscopic tool 220 towards the polyp to be debrided causing the inner blade 450 to debride the polyp, causing portions of the debrided polyp to lie in the vicinity around the area where the polyp had grown. The operator may then de-actuate the turbine assembly and actuate suction through the suction conduit 418. The operator may then bring the inner blade close to the cut polyp causing the cut polyp to be retrieved through the suction conduit 418. In various embodiments, the suction component of the endoscopic tool may be actuated while the debriding component is actuated, thereby allowing any debrided material to be retrieved by the suction component.

Although the above embodiment houses a debriding component that utilizes a turbine assembly, the scope of the present disclosure is not limited to such embodiments. Rather, it should be appreciated by those skilled in the art that the debriding component may be manually operated or may utilize any other means of debriding a polyp such that the debrided polyps are capable of being retrieved from the surgical site via the suction conduit described above. Accordingly, examples of debriding components may include, but are not limited to, snips, blades, saws, or any other sharp tools that may or may not be driven by a turbine assembly. It should be appreciated that using a debriding component that is able to cut a polyp into small enough pieces may be desirable such that the cut pieces may be retrieved via the suction conduit without having to remove the endoscopic tool from the endoscope.

The geometry and assembly of the turbine assembly for rotating at least one of the cutting tool blades may be based on fluid dynamics. Bernoulli's equation can be used to explain the conversion between fluid pressure and the fluid velocity. According to this equation, the fluid velocity is related to the initial fluid pressure by the equation:

$$V = \sqrt{2 * \frac{P}{D}}$$

where V is Velocity, P is Pressure, and D is Mass density.

In order for the fluid to reach the calculated velocity, the fluid can be developed at the point of exit such that the channel through which the fluid is flowing meets an empirically determined L/D ratio of 2, where 'D' is the wetted diameter of the flow and the 'L' is the length of the channel.

To further understand the interaction of the rotor blades and the fluid, it is assumed that the rotor blade is made so that the air jet impinges the rotor blade on a plane. The equation of linear momentum can be applied to find the forces generated:

$$\sum F = \frac{d}{dt}\left(\iiint Vp * dVol.\right) + \sum (\dot{m}V)_{out} - \sum (\dot{m}V)_{in}$$

where: m is the mass flow of the impinging air jet, and Vis Volume.

Assuming that the control volume remains constant (volume between blades), the force created on the blade can be solved for:

$$\Sigma F = \dot{m}(V_{out} - V_{in})$$

The quantity $V_{out}$ and $V_{in}$ are the same in an impulse turbine, the momentum change being created by the changing direction of the fluid only. The mass flow $\dot{m}$ is defined by the pump that is to be specified. The actual numerical value also needs to account for the velocity of the rotor. So finally, the force generated by a single blade-air jet interaction is:

$$\Sigma F = \dot{m}(V_{jet} - V_{rotor}) - (V_{jet} - V_{rotor})\cos\theta$$

$$\Sigma F = \dot{m}(V_{jet} - V_{rotor})(1 - \cos\theta)$$

where 'θ' is the difference of the angle between the incoming air jet to that of the exiting air jet. Thought theoretically, the maximum amount of torque can be generated by a 'θ' value of 180°, but doing so will actually send the incoming jet onto the back of the following blade. Accordingly, the angle is best given a design value 15° to 20° below 180 to allow a fluid a clean exit. Finally, the force can be defined into a rotational torque:

$$\Sigma T = (\dot{m}/r)(V_{jet} - V_{rotor})(1 - \cos\theta)$$

A second force that must be considered comes from redirecting the air jet from the nozzle into the turbine wheel. To power the turbine, the air jet must he turned 90° into the direction of the blades from the direction of the air jet. The turning of the air jet will create a force on the stationary housing that is a function of the jet velocity, which in turn is proportional to the applied pressure:

$$\Sigma F = \dot{m}V_{jet}$$

This force must be reacted by the connection between the housing and the endoscope, a failure to do so can result in the ejection of the turbine assembly during operation.

Computational analyses based on Finite Element Methods (FEM) reveal that the areas where the greatest stresses are found are located near the root of the blade where a sharp corner is located. The design of air input channel can be simplified by the existing air nozzle channel in endoscope. The air nozzle in existing endoscopes directs pressurized air across objective lens to remove moisture and also provides distension of a cavity being examined or directs pressurized water across objective lens to clear debris.

Referring now to FIG. 4B, a perspective view diagram of the endoscopic tool coupled to the endoscope illustrating the various conduits associated with the endoscopic tool is shown. In particular, the pneumatic air entry conduit 412 is shown supplying pressurized air to the rotor assembly, while the pneumatic air exit conduit 412 (not shown in this view) removes the air from the rotor assembly to outside the endoscope 100. The irrigation channel 416 is shown to carry irrigation fluid into the endoscopic tool 220, where the irrigation fluid enters into the suction conduit 418, which carries material from within the patient's body to a collection component outside the endoscope. As shown in FIG. 4B, the irrigation fluid may enter the suction conduit 418 at an irrigation fluid entry opening 419. It should be appreciated that the placement of the irrigation fluid entry opening 419 may be placed anywhere along the suction conduit. Due to the suction force being applied to the suction conduit, irrigation fluid may be forced into the suction conduit without the risk of the materials flowing in the suction conduit from flowing outside the suction conduit through the irrigation fluid entry opening 419. Moreover, in some embodiments, the irrigation channel may only supply irrigation fluid to the endoscopic tool while suction is being applied to the suction conduit.

Figure 5:
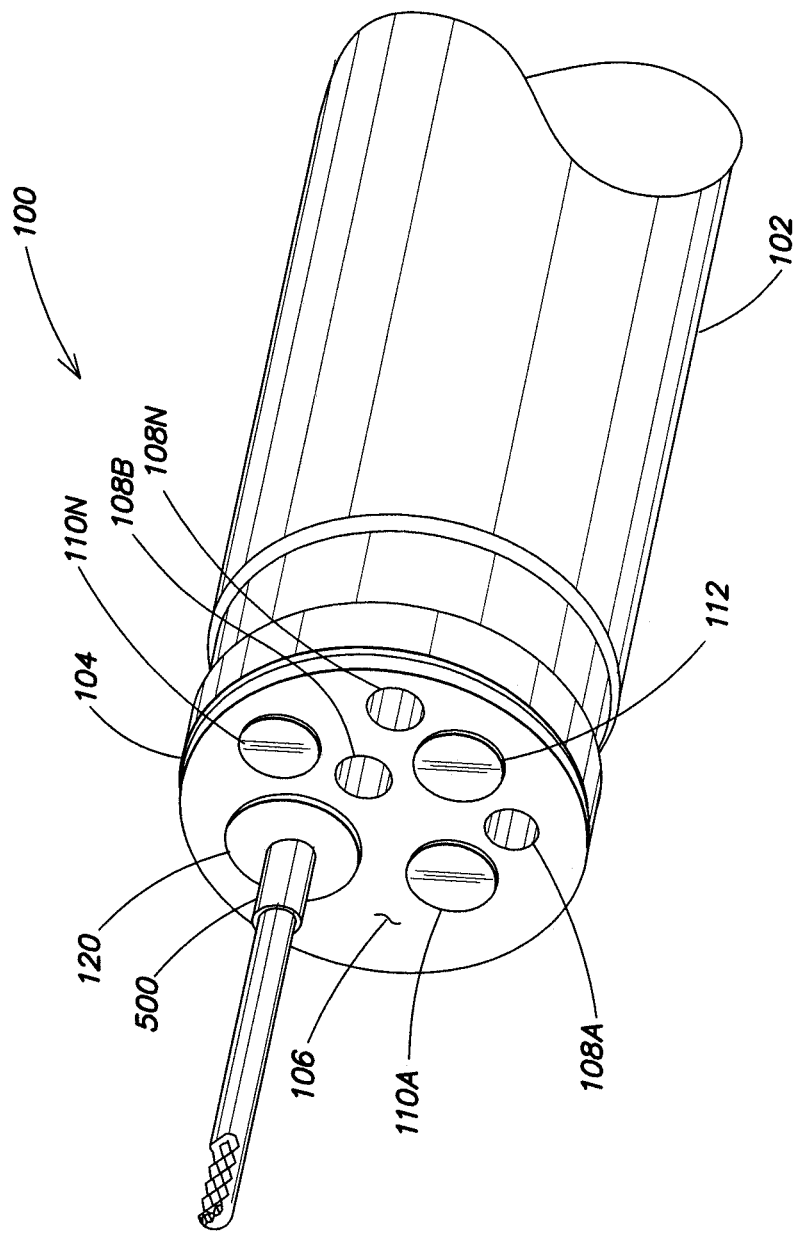
FIG. 5 illustrates a side perspective view of another alternate endoscopic tool coupled with the endoscope shown in FIG. 1 according to embodiments of the present disclosure.

FIG. 5 illustrates a side perspective view of another alternate endoscopic tool coupled with the endoscope shown in FIG. 1 according to embodiments of the present disclosure. The add-on endoscopic tool 500 is sized to couple with the walls defining the instrumentation channel 120 of the tip 104 of the endoscope 100. In various embodiments, the add-on endoscopic tool 500 may be removably attached to the instrumentation channel 120 of the endoscope 100 at the tip 104 of the endoscope 104 by way of an interference fit or a press fit. In other embodiments, the add-on endoscopic tool 500 may be coupled to the endoscope 100 using other attachment means known to those skilled in the art.

Figure 6:
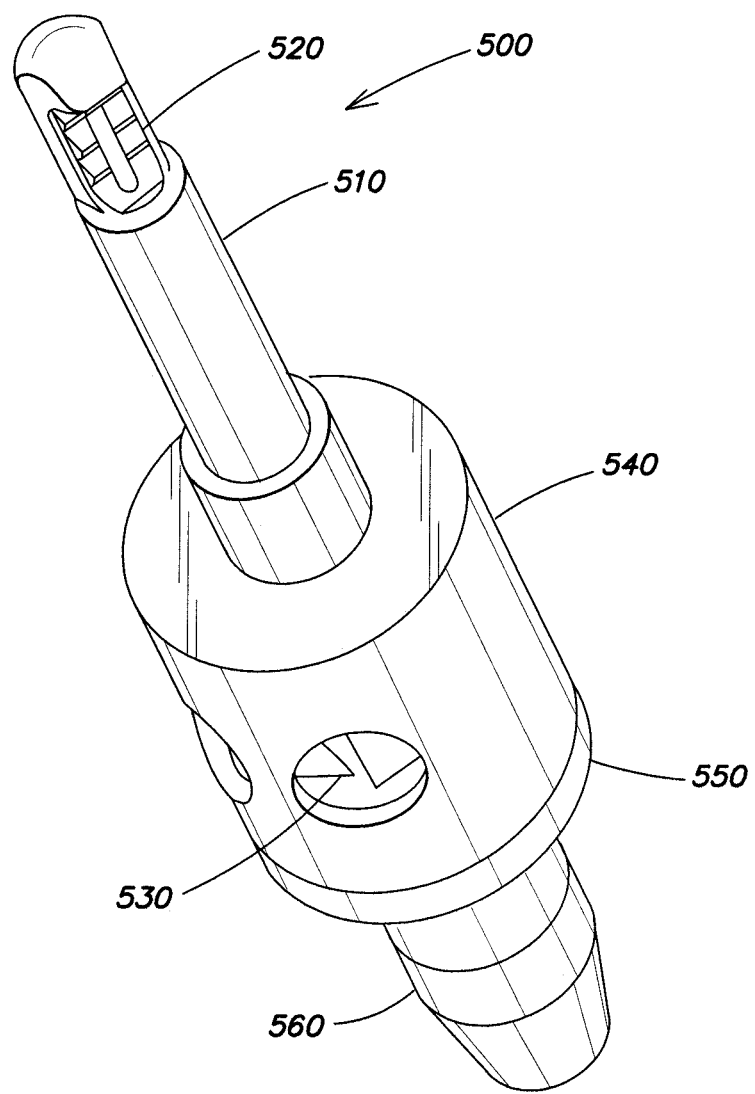
FIG. 6 illustrates an enlarged view of an alternate endoscopic tool according to embodiments of the present disclosure.
Figure 7:
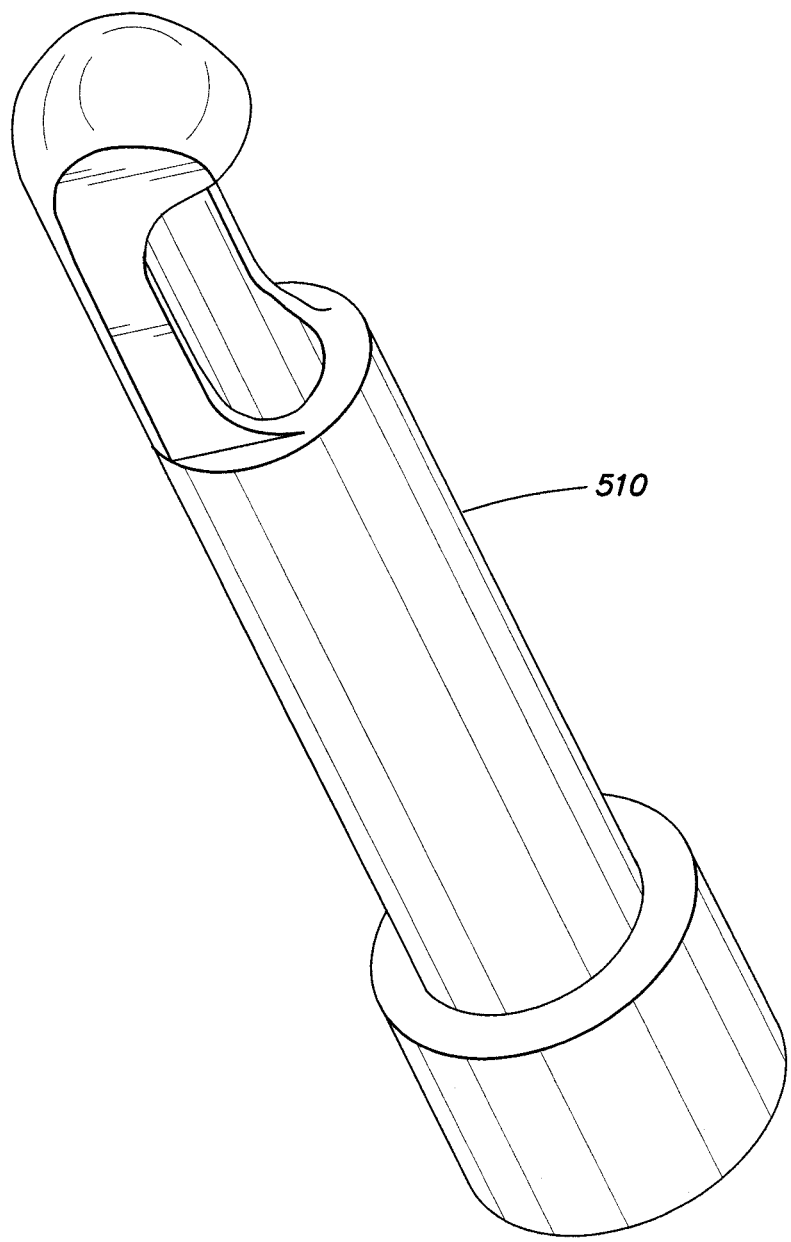
FIG. 7 illustrates a perspective view of an outer blade of a cutting tool of the endoscopic tool shown in FIG. 6 according to embodiments of the present disclosure.
Figure 8:
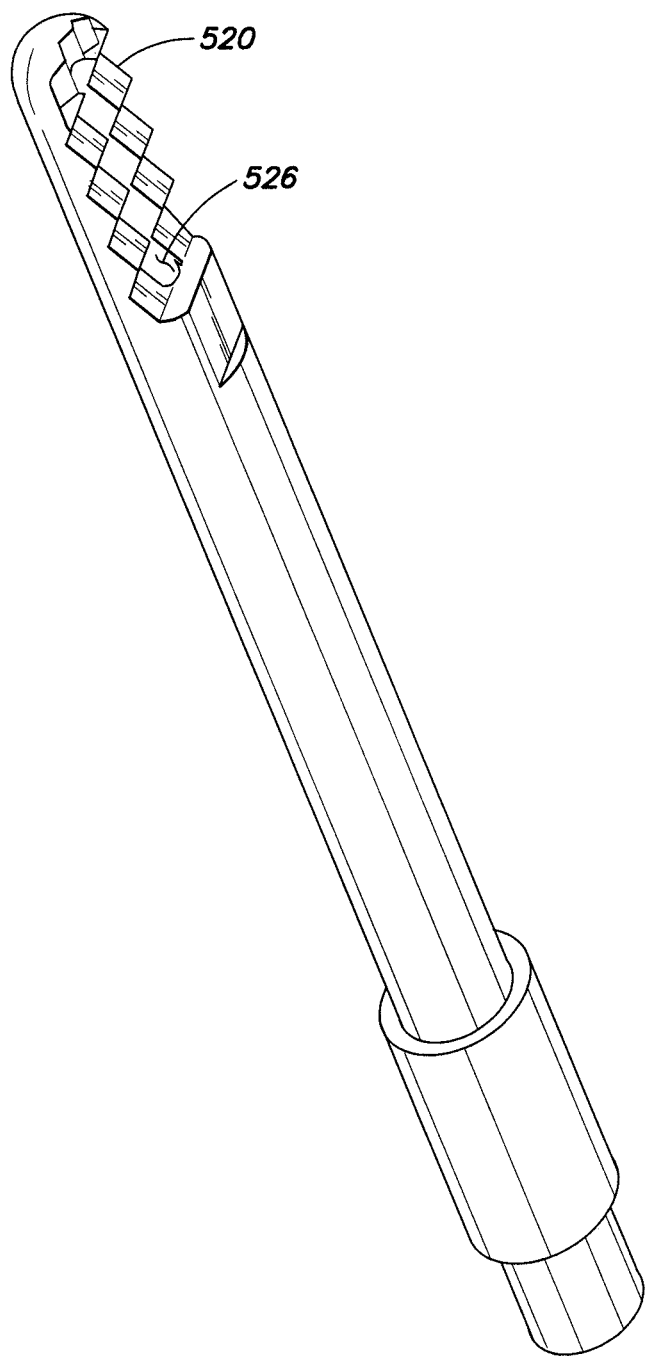
FIG. 8 illustrates a perspective view of an inner blade of the cutting tool of the endoscopic tool shown in FIG. 6 according to embodiments of the present disclosure.
Figure 9:
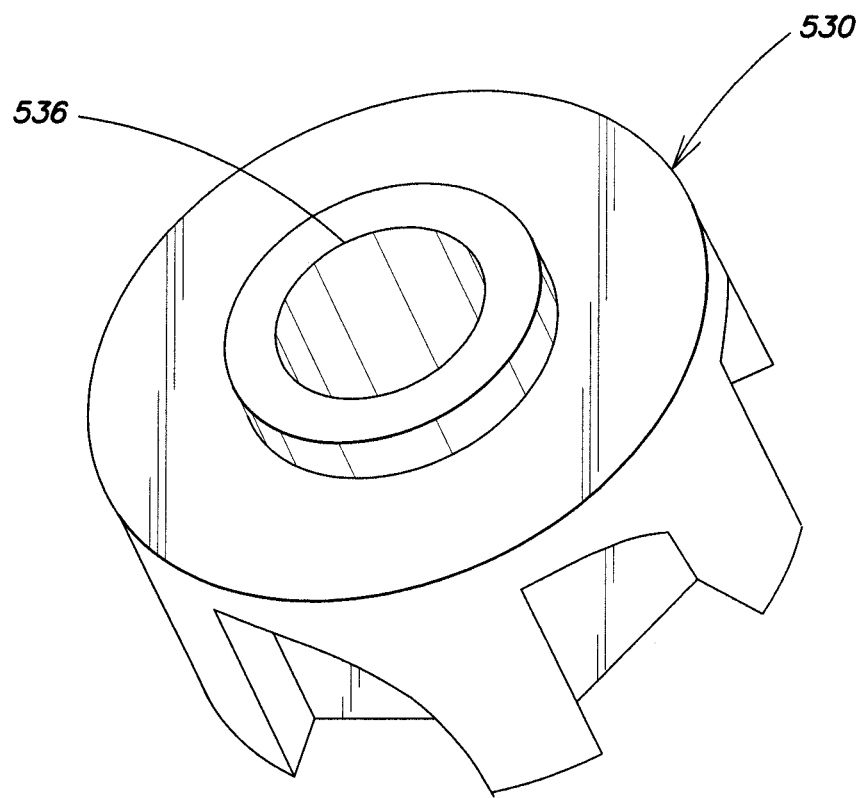
FIG. 9 illustrates a perspective view of a rotor of the endoscopic tool shown in FIG. 6 according to embodiments of the present disclosure.

Referring now to FIG. 6, an enlarged view of the add-on endoscopic tool 500 is shown. The add-on endoscopic tool includes an outer blade or support member 510, an inner blade 520 disposed within the outer blade 510, a rotor 530 coupled to the inner blade 520 and encompassed by a casing 540. The casing is coupled to a cap 550, which is further coupled to a connector 560. In some embodiments, the connector 560 may be sized to engage with the inner diameter of the instrumentation channel 120 of the endoscope 100. In alternate embodiments, any other component of the endoscopic tool may be configured to engage with the endoscope 100 in such a manner as to secure the endoscopic tool to the instrumentation channel 120.

FIGS. 7-12 illustrate perspective views of the individual components of the add-on endoscopic tool shown in FIG. 6 according to embodiments of the present disclosure. In contrast to the endoscopic tool 220 disclosed with respect to FIGS. 1-4, the add-on endoscopic tool 500 may be adapted to fit within a first end of instrumentation channel 120 of the endoscope 100.

In various embodiments, a second end of the instrumentation channel 120 may be coupled to a vacuum source, which causes material to be suctioned through the instrumentation channel 120. A suction conduit extends from the vacuum source through the instrumentation channel of the endoscope, and further through the connector 560, the cap 550, and the rotor 530, to a first end of the inner blade 520, which has an opening defined by the inner diameter of the inner blade 520. It should be appreciated that the connector 560, the cap 550, the casing 540, and the rotor 530 have respective center bores 566, 556, 546 and 536 that are aligned such that materials are allowed to flow from the opening of the inner blade 520 to the vacuum source via the second end of the instrumentation channel 120.

Figure 10:
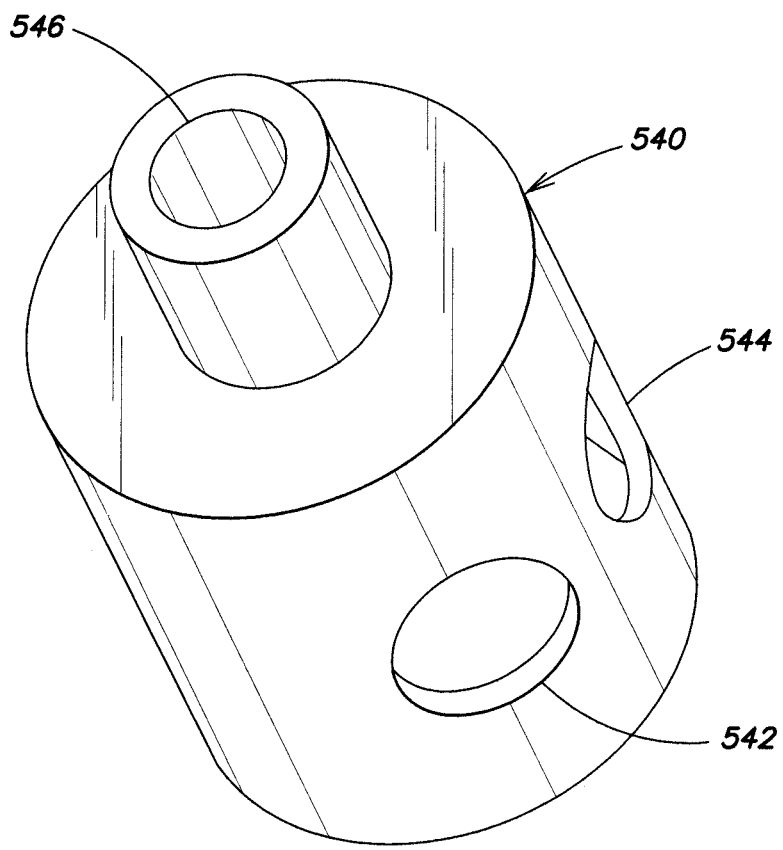
FIG. 10 illustrates a perspective view of a casing of the endoscopic tool shown in FIG. 6 according to embodiments of the present disclosure.
Figure 11:
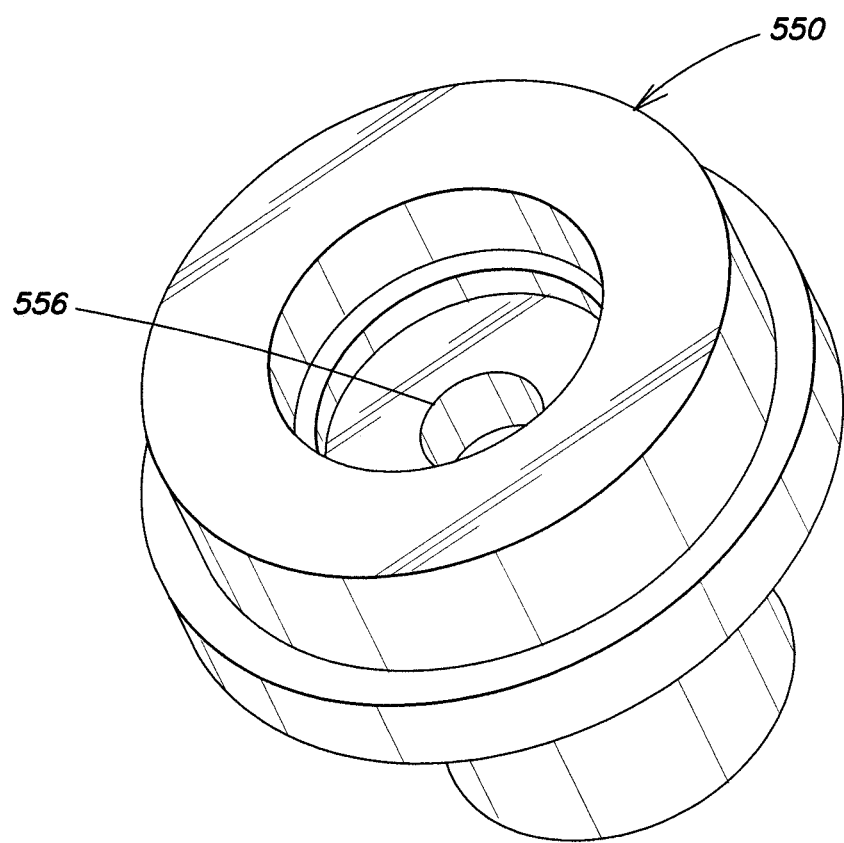
FIG. 11 illustrates a perspective view of a cap of the endoscopic tool shown in FIG. 6 according to embodiments of the present disclosure.
Figure 12:
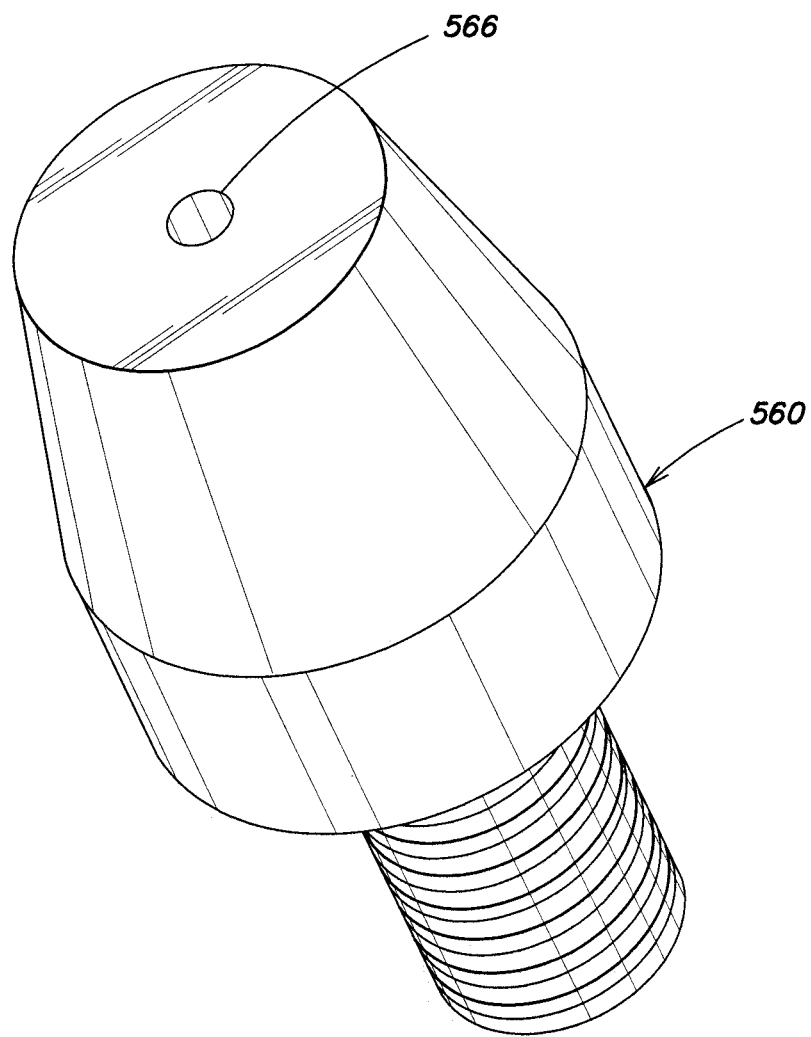
FIG. 12 illustrates a perspective view of a coupling member of the endoscopic tool shown in FIG. 6 according to embodiments of the present disclosure.

In addition, the casing 540 of the add-on endoscopic tool 500 includes a pneumatic air entry port 542 and a pneumatic air exit port 544 as shown in FIG. 10. The pneumatic air entry port 542 may be adapted to receive compressed air from a compressed air source through a pneumatic air entry conduit that passes along the length of the endoscope 100 to outside the patient's body, while the pneumatic air exit port 544 may be adapted to vent air that is impinged on the rotor 530 through a pneumatic air exit conduit that passes along the length of the endoscope 100 to outside the patient's body. In this way, the rotor may be actuated by supplying compressed air from the compressed air source, as described above with respect to FIGS. 1-4. It should be appreciated that although the rotor and associated components disclosed herein describe the use of pneumatic air, the rotor may he driven hydraulically. In such embodiments, the pneumatic air conduits may be configured to carry a liquid, such as water, to and from the area around the rotor.

Figure 13:
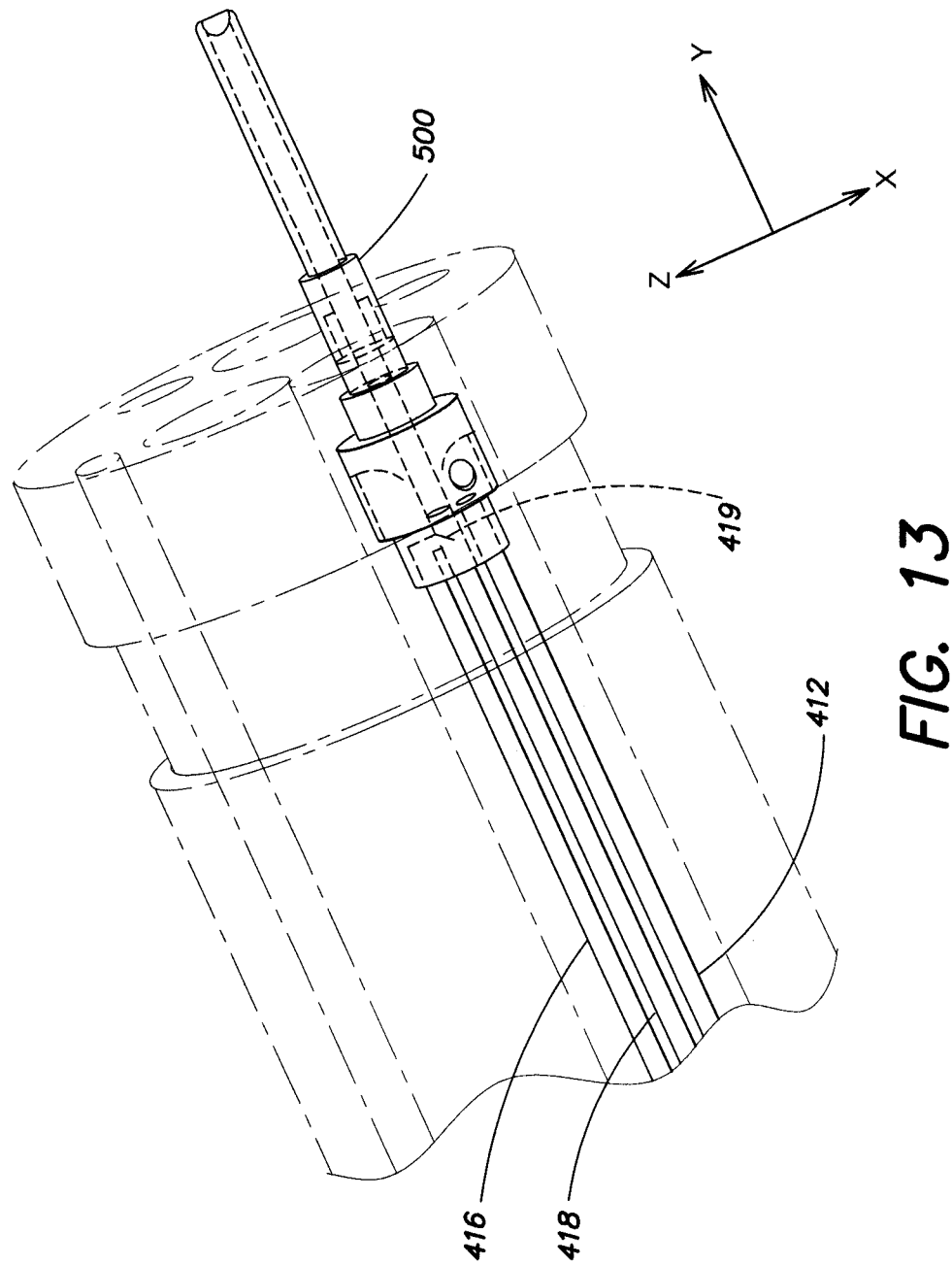
FIG. 13 illustrates a perspective view diagram of the endoscopic tool coupled to the endoscope illustrating the various conduits associated with the endoscopic tool.

Referring now also to FIG. 13, it should be appreciated that the pneumatic air entry and exit conduits may extend from the add-on endoscopic tool to a pneumatic air source through the instrumentation channel 120 of the endoscope 100. In such embodiments, a tubing that includes separate conduits for the pneumatic air entry and exit conduits and the suction conduit may extend from outside the endoscope to the add-on endoscopic tool within the endoscope. The tubing may be capable of being fed through the instrumentation channel of the endoscope and coupled to the add-on endoscopic tool 500. In such embodiments, the add-on endoscopic tool 500 may be configured with an additional component that has predefined channels that couple the respective channels of the tubing with the associated with the pneumatic air entry and exit openings of the add-on endoscopic tool and the suction conduit formed within the add-on endoscopic tool. In addition, an irrigation fluid channel may also be defined within the tubing such that irrigation fluid may be supplied to the add-on endoscopic tool 500, from where the irrigation fluid is diverted into the suction conduit.

In various embodiments, the tip of the outer blade 510 may be sharp and may cause discomfort to the patient while entering a cavity of the patient's body. As such, a guard structure (not shown), such as a gel cap or other similar structure, may be attached to the outer blade prior to inserting the add-on endoscopic tool into the patient's body to prevent injuries from the outer blade contacting a surface of the patient's body. Once the endoscopic tool is inserted in the patient's body, the guard structure may be released from the outer blade 510. In various embodiments, the guard structure may dissolve upon entering the patient's body.

Figure 14:
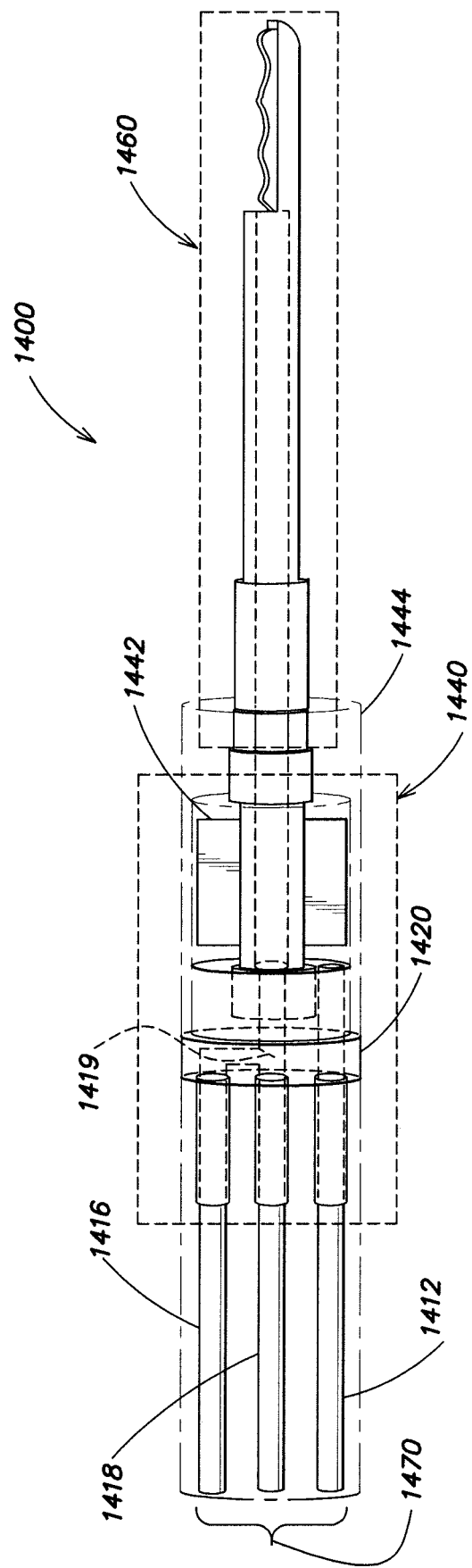
FIG. 14 illustrates another perspective view diagram of the endoscopic tool coupled to the endoscope illustrating the various conduits associated with the endoscopic tool.

Referring now to FIG. 14, an improved endoscope having a built in polyp removal assembly is shown according to embodiments of the present disclosure. The improved endoscope 1400 may be similar to conventional endoscopes in many aspects, but may differ in that the improved endoscope may include a built in polyp removal assembly 1440 within an instrumentation channel of the endoscope 1400. The polyp removal assembly 1440 may include a turbine assembly having a rotor 1442 with rotor blades sealed in a casing 1444 that has one or more inlet and outlet ports for allowing either pneumatic or hydraulic fluid to actuate the rotor 1442. The inlet ports may be designed such that the fluid may interact with the rotor blades at a suitable angle to ensure that the rotor can be driven at desired speeds.

In addition, the polyp removal assembly 1440 may be coupled to a connector 1420, which is configured to couple the polyp removal assembly 1440 to a tubing 1470. The tubing 1470 may include a pneumatic air entry conduit 1412, a pneumatic air exit conduit (not shown), an irrigation fluid conduit 1416 and a suction conduit 1418 that passes through the center of the turbine assembly. The tubing 1440 may be sized such that the tubing 1440 can be securely coupled to the connector 1420 such that one or more of the conduits of the tubing 1440 are coupled to corresponding conduits within the connector 1440. The connector 1420 may be designed to include an irrigation fluid entry opening 419, which allows irrigation fluid to pass into the suction conduit 1418 of the tubing 1440 when the tubing is coupled to the connector.

The turbine assembly of the endoscope 1400 may be configured to couple with a removable debriding assembly 1460, which includes a spindle and a cannula, in a manner that causes the debriding assembly to be operational when the turbine assembly is operating.

In other embodiments of the present disclosure, an endoscope may be designed to facilitate debriding one or more polyps and removing the debrided material associated with the polyps in a single operation. In various embodiments, the endoscope may include one or more separate channels for removing debrided material, supplying irrigation fluid, and supplying and removing at least one of pneumatic or hydraulic fluids. In addition, the endoscope may include a debriding component that may be fixedly or removably coupled to one end of the endoscope. In various embodiments, based on the operation of the debriding component, a separate debriding component channel may also be designed for the debriding component. In addition, the endoscope may include a light and a camera. In one embodiment, the endoscope may utilize existing channels to supply pneumatic or hydraulic fluids to the actuator of the endoscopic tool for actuating the debriding component. For instance, in the endoscope shown in FIG. 1, the water channels 108A-N may be modified to supply fluids to the actuator pneumatically or hydraulically. In such embodiments, the endoscopic tool may include a connector having a first end capable of being coupled to an opening associated with existing channels 108 of the endoscope, while another end of the connector is exposed to an opening at the actuator.

In various embodiments of the present disclosure, the endoscopic tool may further be configured to detect the presence of tissue or muscle. This may be useful for physicians to take extra precautions to prevent bowel perforations while debriding polyps. In some embodiments, the endoscopic tool may be equipped with an electrical sensor that can communicate with a sensor processing component outside the endoscope to determine if a particular region of the patient's body is made from tissue or muscle. The sensor may gather temperature information as well as density information and provide signals corresponding to such to the sensor processing unit, which can determine from the signals, if the particular region is made from tissue or muscle.

In addition, the endoscopic tool may be equipped with an injectable dye component through which a physician may mark a particular region within the patient's body. In other embodiments, the physician may mark a particular region utilizing the debriding component, without the use of an injectable dye.

Although the present disclosure discloses various embodiments of an endoscopic tool, including but not limited to a tool that may be attached to the tip of the endoscope, and a tool that may be fed through the length of the endoscope, the scope of the present disclosure is not intended to be limited to such embodiments or to endoscopic tools in general. Rather, the scope of the present disclosure extends to any device that may debride and remove polyps from within a patient's body using a single tool. As such, the scope of the present disclosure extends to improved endoscopes that may be built with some or all of the components of the endoscopic tools described herein. For instance, an improved endoscope with a built in turbine assembly and configured to be coupled to a debriding component is also disclosed herein. Furthermore, the endoscope may also include predefined conduits that extend through the length of the endoscope such that only the suction conduit may be defined by a disposable tubing, while the air entry and exit conduits and the irrigation conduit are permanently defined within the improved endoscope. In other embodiments, the suction conduit is also predefined but made such that the suction conduit may be cleaned and purified for use with multiple patients. Similarly, the debriding component may also be a part of the endoscope, but also capable of being cleaned and purified for use with multiple patients. Furthermore, it should be understood by those skilled in the art that any or all of the components that constitute the endoscopic tool may be built into an existing endoscope or into a newly designed endoscope for use in debriding and removing polyps from within the patients body.

Figure 15:
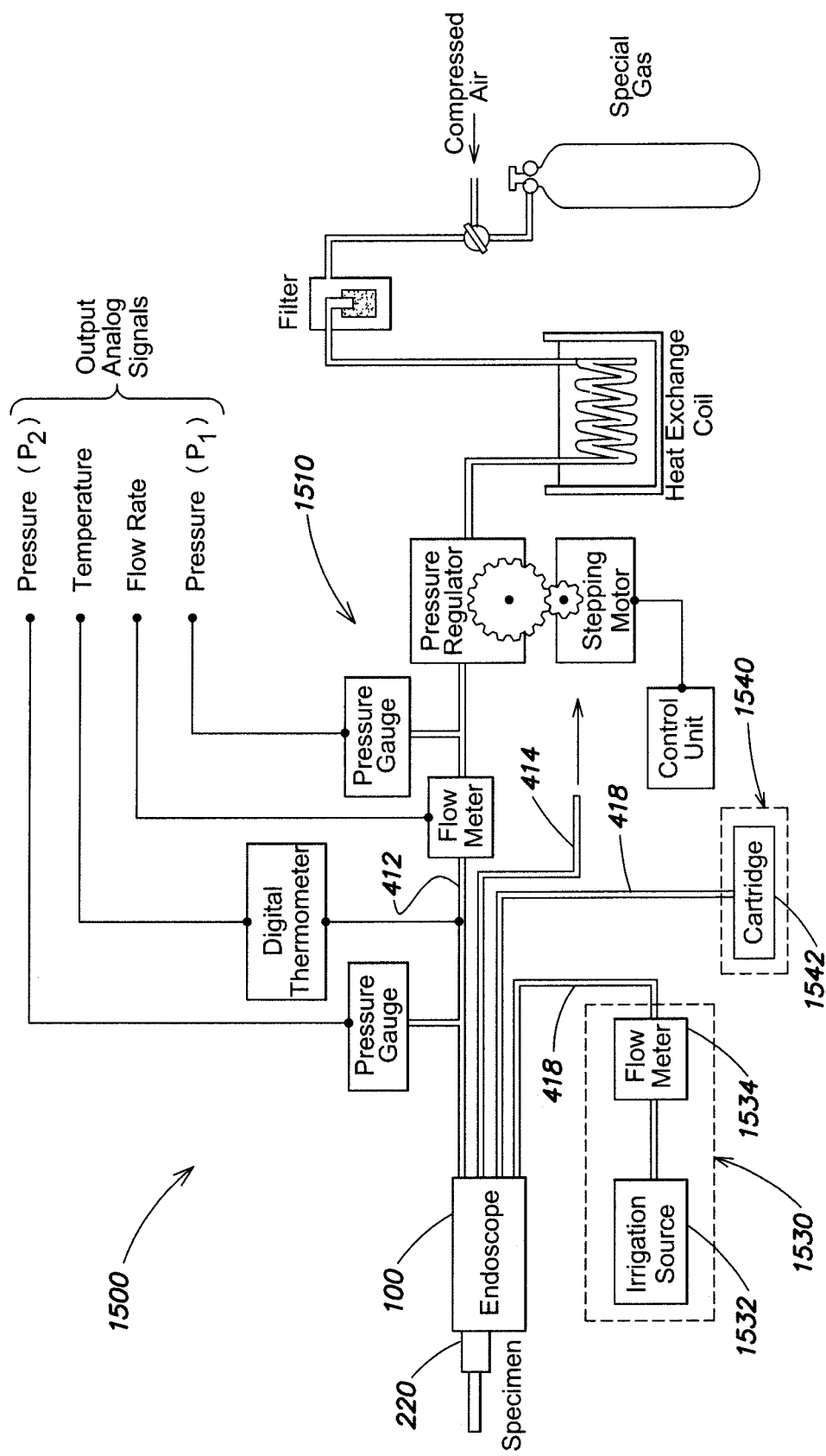
FIG. 15 is a conceptual system architecture diagram illustrating various components for operating the endoscopic tool according to embodiments of the present disclosure.

Referring now to FIG. 15, a conceptual system architecture diagram illustrating various components for operating the endoscopic tool according to embodiments of the present disclosure is shown. The endoscopic system 1500 includes an endoscope 100 fitted with an endoscopic tool 220, and which may be coupled to an air supply measurement system 1510, an irrigation system 1530 and a polyp removal system 1540. As described above, the tubing that extends within the endoscope 100 may include one or more pneumatic air entry conduits 412 and one or more pneumatic air exit conduits 414. The pneumatic air entry conduits 412 are coupled to the air supply measurement system 1510, which includes one or more sensors, gauges, valves, and other components to control the amount of gas, such as air, being supplied to the endoscope 100 to drive the rotor 440. In some embodiments, the amount of air being supplied to the rotor 440 may be controlled using the air supply measurement system 1510. Furthermore, delivery of the air to actuate the rotor 440 may be manually controlled by the physician using the endoscope 100. In one embodiment, the physician may use a foot pedal or a hand-actuated lever to supply air to the rotor 440.

The pneumatic air exit conduit 414, however, may not be coupled to any component. As a result, air exiting from the rotor 440 may simply exit the endoscope via the pneumatic air exit conduit 414 into the atmosphere. In alternate embodiments, the pneumatic air exit conduit 414 may be coupled to the air supply measurement system 1510 such that the air exiting the pneumatic air exit conduit 414 is supplied back to the rotor via the pneumatic air entry conduit 412. It should be appreciated that a similar setup may be used for a hydraulically driven turbine system.

The endoscope 100 may also be coupled to the irrigation system 1530 via the irrigation fluid conduit 416. The irrigation system 1530 may include a flow meter 1534 coupled to an irrigation source 1532 for controlling the amount of fluid flowing from the irrigation source 1532 to the endoscope 100.

As described above, the endoscope 100 may also include a suction conduit 418 for removing polyps from within the patient's body. The suction conduit 418 may be coupled to the polyp removal system 1540, which may be configured to store the polyps. In various embodiments, the physician may be able to collect samples in one or more cartridges 1542 within the polyp removal system 1540 such that the removed polyps can be tested individually.

In various embodiments of the present disclosure, an endoscope, comprises a first end and a second end separated by a flexible housing, an instrumentation channel extending from the first end to the second end, and an endoscopic tool comprising a debriding component and a sample retrieval conduit disposed within the instrumentation channel. The endoscopic tool may further include a flexible tubing in which the sample retrieval conduit is partially disposed, the flexible tubing extending from the first end to the second end of the endoscope. The flexible tubing may also include a pneumatic air entry conduit and a fluid irrigation conduit. In various embodiments, the debriding component may include a turbine assembly and a cutting tool. In various embodiments in which the endoscope is configured to have a built in endoscopic tool, the instrumentation channel may have a diameter that is larger than the instrumentation channels of existing endoscopes. In this way, larger portions of debrided material may be suctioned from within the patient's body without clogging the suction conduit.

In other embodiments, an endoscope may include a first end and a second end separated by a flexible housing; an instrumentation channel extending from the first end to the second end; and an endoscopic tool coupled to the instrumentation channel at the first end of the endoscope, the endoscopic tool comprising a debriding component and a sample retrieval conduit partially disposed within the instrumentation channel. In some embodiments, the endoscopic tool may be removably attached to the endoscopic tool.

In other embodiments of the present disclosure, an endoscopic system, includes an endoscope comprising a first end and a second end separated by a flexible housing and an instrumentation channel extending from the first end to the second end and an endoscopic tool coupled to the instrumentation channel at the first end of the endoscope. The endoscopic tool may include a debriding component and a flexible tubing having a length that is greater than the length of the endoscope. Moreover, the flexible tubing may include a sample retrieval conduit, an pneumatic air entry conduit, and a fluid irrigation conduit, a disposable cartridge configured to couple with the sample retrieval conduit proximal the second end of the endoscope, a pressurized air source configured to couple with the pneumatic air entry conduit proximal the second end of the endoscope, and a fluid irrigation source configured to couple with the fluid irrigation conduit proximal the second end of the endoscope. In various embodiments, the endoscope may also include at least one camera source and at least one light source. In some embodiments of the present disclosure, the pneumatic air entry conduit supplies pressurized air to a turbine assembly of the debriding component proximal the first end of the endoscope and the fluid irrigation conduit supplies irrigation fluid to the sample retrieval conduit proximal the first end of the endoscope.

The present disclosure is illustratively described above in reference to the disclosed embodiments. Various modifications and changes may be made to the disclosed embodiments by persons skilled in the art without departing from the scope of the present disclosure as defined in the appended claims.

What is claimed is:

1. An endoscopic instrument inserted within an instrument channel of an endoscope, the endoscopic instrument comprising:
a power-driven instrument head configured to cut tissue at a site within a subject, the power-driven instrument head having a first proximal end;
a body comprising a powered actuator coupled to the first proximal end of the power-driven instrument head and configured to drive the power-driven instrument head, and
the body further comprising a flexible tubing coupled to the powered actuator such that the powered actuator is positioned between the power-driven instrument head and the flexible tubing, the flexible tubing and the powered actuator configured to be positioned within a distal portion of the instrument channel of the endoscope during use while the distal portion of the instrument channel is within a cavity of the subject.

2. The endoscopic instrument of claim 1, further comprising an engagement assembly, the engagement assembly configured to contact walls of the instrument channel of the endoscope when actuated.

3. The endoscopic instrument of claim 2, wherein the engagement assembly includes a compliant ring structure configured to be deformed.

4. The endoscopic instrument of claim 1, wherein the powered actuator includes at least one of an electric motor, a tesla rotor, and a vane rotor.

5. The endoscopic instrument of claim 1, further comprising an energy storage component configured to power the powered actuator.

6. The endoscopic instrument of claim 1, wherein the endoscopic instrument has an outer diameter that is less than about 5 mm.

7. The endoscopic instrument of claim 1, wherein the powered actuator is one of a hydraulically powered actuator or a pneumatically powered actuator, and wherein the flexible tubing includes a fluid inlet tubular member configured to supply fluid to actuate the powered actuator and a fluid outlet tubular member configured to remove the fluid being supplied to actuate the powered actuator.

8. The endoscopic instrument of claim 1, wherein the powered actuator is one of a hydraulically powered actuator, a pneumatically powered actuator or an electrically powered actuator.

9. The endoscopic instrument of claim 1, wherein the power-driven instrument head includes an outer structure and a cutting shaft disposed within the outer structure, the cutting shaft coupled to the powered actuator and configured to rotate relative to the outer structure when the powered actuator is actuated.

10. The endoscopic instrument of claim 9, wherein the cutting shaft includes a hollow tubing and a material entry port to receive the cut tissue.

11. The endoscopic instrument of claim 1, wherein the flexible tubing is at least 40 times as long as the power-driven instrument head.

12. An endoscopic tool, comprising:
a cutting tool having a first distal end and a first proximal end, the first distal end of the cutting tool defining a material entry port configured to receive tissue; a turbine assembly configured to drive the cutting tool, the turbine assembly disposed within a portion of an instrument channel of an endoscope that is inserted within a cavity of a subject;
a flexible tubing having a second proximal end defining a material exit port, the flexible tubing including: a fluid entry conduit configured to supply fluid to the turbine assembly, and a fluid exit conduit configured to remove the fluid from the turbine assembly.

13. The endoscopic tool of claim 12, wherein the cutting tool comprises a cylindrical or part-cylindrical inner blade disposed within an outer blade, and an outer structure and a cutting shaft disposed within the outer structure, the cutting shaft coupled to the cutting tool and configured to rotate relative to the outer structure when the cutting tool is driven.

14. The endoscopic tool of claim 13, wherein the turbine assembly comprises a fluid driven rotor or vacuum driven rotor and means for introducing feeding fluid to drive the fluid driven rotor or the vacuum driven rotor.

15. The endoscopic tool of claim 14, wherein the fluid driven rotor or the vacuum driven rotor is coupled to the inner blade.

16. The endoscopic tool of claim 14, wherein the turbine assembly further comprises a hydraulic fluid exit conduit for removing irrigation fluid from the turbine assembly and an irrigation fluid conduit for supplying the irrigation fluid to the turbine assembly.

17. The endoscopic tool of claim 12, further comprising a connector that connects the endoscopic tool to the instrument channel of the endoscope.

18. The endoscopic tool of claim 12, wherein the cutting tool comprises a rotor and a casing, the casing having an entry port for supplying the fluid to the turbine assembly and an exit port for removing the fluid from the turbine assembly.

19. The endoscopic tool of claim 12, further comprising a first controller for selectively supplying the fluid to the cutting tool.

\* \* \* \* \*